US011806432B2

(12) United States Patent
Randolph et al.

(10) Patent No.: US 11,806,432 B2
(45) Date of Patent: *Nov. 7, 2023

(54) COMPOSITIONS, METHODS AND USES FOR THERMALLY STABLE MULTI-TARGETED ANTIGENS

(71) Applicant: THE REGENTS OF THE UNIVERSITY OF COLORADO, A BODY CORPORATE, Denver, CO (US)

(72) Inventors: Theodore Randolph, Niwot, CO (US); Robert Garcea, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/665,285

(22) Filed: Feb. 4, 2022

(65) Prior Publication Data

US 2022/0175907 A1 Jun. 9, 2022

Related U.S. Application Data

(63) Continuation of application No. 16/146,686, filed on Sep. 28, 2018, now Pat. No. 11,273,127, which is a continuation-in-part of application No. 15/309,169, filed as application No. PCT/US2015/029529 on May 6, 2015, now abandoned.

(60) Provisional application No. 61/989,365, filed on May 6, 2014.

(51) Int. Cl.
| | | |
|---|---|---|
| *A61K 9/16* | (2006.01) | |
| *A61K 9/19* | (2006.01) | |
| *C12N 7/00* | (2006.01) | |
| *A61K 39/12* | (2006.01) | |
| *A61K 39/295* | (2006.01) | |
| *A61K 45/06* | (2006.01) | |
| *A61K 39/00* | (2006.01) | |

(52) U.S. Cl.
CPC .............. *A61K 9/19* (2013.01); *A61K 9/1623* (2013.01); *A61K 9/1694* (2013.01); *A61K 39/12* (2013.01); *A61K 39/295* (2013.01); *A61K 45/06* (2013.01); *C12N 7/00* (2013.01); *A61K 2039/5252* (2013.01); *A61K 2039/5258* (2013.01); *A61K 2039/55505* (2013.01); *A61K 2039/55572* (2013.01); *C12N 2710/20034* (2013.01); *C12N 2710/20063* (2013.01); *C12N 2710/20071* (2013.01)

(58) Field of Classification Search
None
See application file for complete search history.

(56) References Cited

U.S. PATENT DOCUMENTS

| | | | |
|---|---|---|---|
| 6,306,404 B1 | 10/2001 | Laposta et al. | |
| 6,592,872 B1 | 7/2003 | Klimpel et al. | |
| 7,763,450 B2 | 7/2010 | Robinson et al. | |
| 8,444,991 B2 | 5/2013 | Randolph et al. | |
| 8,512,679 B2 | 8/2013 | Hyde et al. | |
| 8,808,710 B2 | 8/2014 | Randolph et al. | |
| 9,731,020 B2 | 8/2017 | Harel et al. | |
| 9,744,227 B2 | 8/2017 | Bronshtein | |
| 10,532,093 B2 | 1/2020 | Gill et al. | |
| 2003/0049268 A1 | 3/2003 | Artois et al. | |
| 2004/0042972 A1 | 3/2004 | Truong-Le et al. | |
| 2005/0226893 A1 | 10/2005 | Juneau et al. | |
| 2005/0244432 A1 | 11/2005 | Castillo et al. | |
| 2012/0141528 A1 | 6/2012 | Coffey et al. | |
| 2013/0309273 A1 | 11/2013 | Hassett et al. | |
| 2014/0044717 A1 | 2/2014 | Kranz et al. | |
| 2014/0127260 A1 | 5/2014 | Chintala et al. | |
| 2015/0250869 A1 | 9/2015 | Sene et al. | |

(Continued)

FOREIGN PATENT DOCUMENTS

| | | |
|---|---|---|
| EP | 0156242 A2 | 2/1985 |
| WO | 2008118691 A3 | 10/2008 |
| WO | 2009108689 A1 | 9/2009 |

(Continued)

OTHER PUBLICATIONS

Zeltins, "Construction and Characterization of Virus-Like Particles: A Review", Mol Biotechnol, (2013), vol. 53, pp. 92-107.

Anchordoquy et al., "Polymers Protect Lactate Dehydrogenase during Freeze-Drying by Inhibiting Dissociation in the Frozen State", Archives of Biochem and Biophysics, vol. 332 (2), (1996):231-238.

Anchordoquy et al., "Maintenance of Quaternary Structure in the Frozen State Stabilizes Lactate Dehydrogenase Turing Freeze-Drying", Archives of Biochem and Biophysics, vol. 390 (1), (2001):35-41.

Clapp et al., "Vaccines with Aluminum-Containing Adjuvants: Optimizing Vaccine Efficacy and Thermal Stability", J. Pharm. Sci., vol. 100 (2), (2011):388-401.

(Continued)

*Primary Examiner* — Nianxiang Zou
(74) *Attorney, Agent, or Firm* — Polsinelli PC

(57) ABSTRACT

Embodiments of the present invention provide for novel compositions and methods for making and using a thermally stable human papilloma virus (HPV) formulation or other stabilized multimeric virus formulation. Certain embodiments concern lyophilizing HPV formulations in the presence or absence of adjuvants. Other embodiments concern lypophilizing HPV capsomere vaccines in order to increase stability of an immunogenic composition against HPV infection for storage, delivery and use. In yet other embodiments, a single immunogenic composition can include a thermally stable formulation of multiple virus serotypes. Yet other embodiments disclosed herein concern multi-targeted antigen complexes lyophilized in formulations of use to prolong stability and/or enhance immunogenicity. Other embodiments concern exposing lyophilized multi-targeted antigen complexes to elevated temperatures to enhance immunogenicity of the antigens of the complex to multiple pathogens.

25 Claims, 21 Drawing Sheets

(56) References Cited

U.S. PATENT DOCUMENTS

Figure 1A:
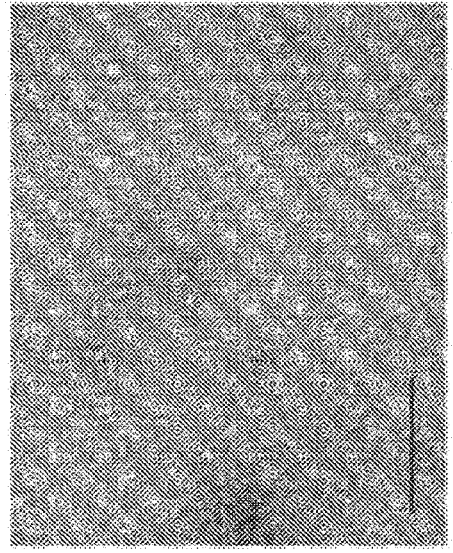

2017/0065707 A1    3/2017    Randolph et al.
2018/0092851 A1    5/2018    Hassett et al.

FOREIGN PATENT DOCUMENTS

WO      2012158978 A1    11/2012
WO      2012177970 A1    12/2012

OTHER PUBLICATIONS

Clausi et al., "Inhibition of Aggregation of Aluminum Hydroxide Adjuvant during Freezing and Drying", J. Pharm. Sci., (2008) vol. 97(6):2049-2061.

Giannini et al., "Enhanced humoral and memory B cellular immunity using HPV 16/18 L1 VLP vaccine formulated with the MPL/aluminium salt combination (AS04) compared to aluminium salt only", Vaccine, vol. 24, (2006):5937-5949.

Hassett et al., "Stabilization of a recombinant ricin toxin A subunit vaccine through lyophilization", EP Journal of Pharm. and Biopharm, vol. 85, (2013):279-286.

Hinrichs et al., "Inulin glasses for the stabilization of therapeutic proteins", International Journal of Pharmaceutics, vol. 215, (2001):163-174.
International Search Report and Written Opinion for PCT/US2015/029529, dated Jun. 15, 2015, 10 pages.
Martins et al., "A review of Maillard reaction in food and implications to kinetic modelling", Trends in Food Science and Technology, vol. 11, (2001):364-373.
Netter et al., "Antigenicity and Immunogenicity of Novel Chimeric Hepatitis B Surface Antigen Particles with Exposed Hepatitis C Virus Epitopes", Journal of Virology, (2001), vol. 75(5):2130-2141.
Patil et al., "Evaluation of monophosphoryl lipid A as adjuvant for pulmonary delivered influenza vaccine.", Journal of Controlled Release, (2014), vol. 174:51-62.
Schellenbacher et al., "Efficacy of RG1-VLP Vaccination against Infections with Genital and Cutaneous Human Papillomaviruses", Journal of Investigative Dermatology (2013), vol. 133:2706-2713.
Shouval, "Hepatitis B vaccines", Journal of Hepatology, (2003), vol. 39:S70-S76.
Wu et al., "Capsomer Vaccines Protect Mice from Vaginal Challenge with Human Papillomavirus", PLoS ONE 6(11): e327141. doi: 10.1371/journal_pone.0027141.
Deschuyteneer, M. et al., "Molecular and structural characterization of the L1 virus-like particles that are used as vaccine antigens in Cervarix, the ASO4-adjuvanted HPC-16 and -18 cervical cancer vaccine," Human Vaccines, vol. 6, No. 5, May 1, 2010, pp. 407-419.
Lang, R. et al. "Rational Design of a Stable, Freeze-Dried Virus-Like Particle-Based Vaccine Formulation," Journal Drug Development and Industrial Pharmacy, vol. 35, No. 1, Oct. 1, 2009, pp. 83-97.

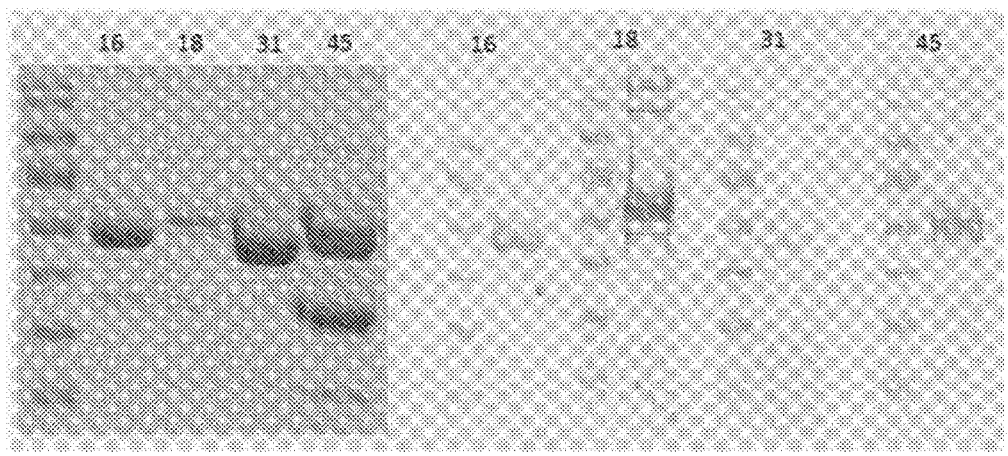
Fig. 13A  SDS PAGE  WESTERN BLOT
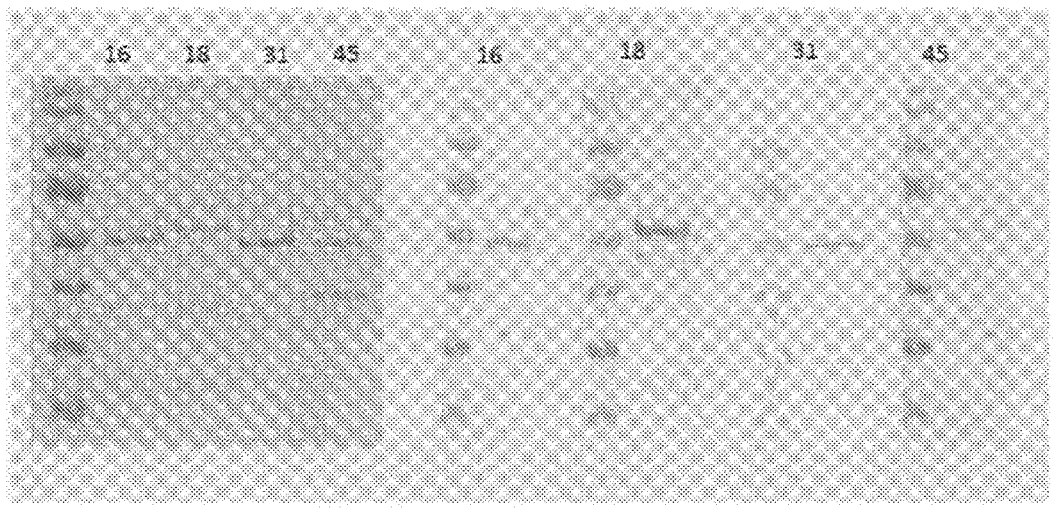
Fig. 13B  SDS PAGE  WESTERN BLOT
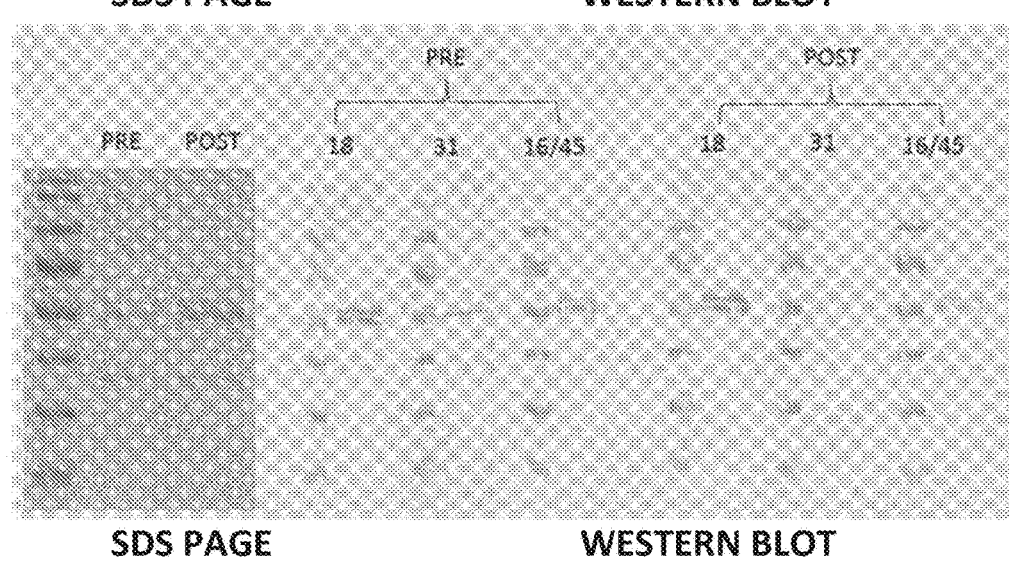
Fig. 13C  SDS PAGE  WESTERN BLOT

| lyophilized RG1-VLP stored at | | HPV16 L1-VLP ELISA Titer | RG1 peptide ELISA Titer |
|---|---|---|---|
| 4°C | 1 day | 12,800 | 12,800 |
| | 1 week | 12,800 | 3,200 |
| | 1 month | 12,800 | 12,800 |
| 20°C | 1 day | 12,800 | 3,200 |
| | 1 week | 12,800 | 3,200 |
| | 1 month | 12,800 | 3,200 |
| 37°C | 1 day | 12,800 | 3,200 |
| | 1 week | 12,800 | 12,800 |
| | 1 month | 51,200 | 3,200 |
| 50°C | 1 day | 204,800 | 12,800 |
| | 1 week | 12,800 | 3,200 |
| | 1 month | 12,800 | 12,800 |
| PBS | | 0 | 0 |
| anti-16 L1-VLP serum | | >800 | n.d. |
| anti-RG1-VLP serum | | n.d. | 800 |
| anti-BPV antibody | | n.d. | 0 |

Fig. 14

Figs. 15A-15B

Pseudovirion-based neutralization assay (PBNA)

A. L1-PBNA

| HPV | immune sera raised against lyophilized RG1-VLP stored at | | | | | | | | | | | | PBS |
|---|---|---|---|---|---|---|---|---|---|---|---|---|---|
| | 4°C 1D | 4°C 1W | 4°C 1M | 20°C 1D | 20°C 1W | 20°C 1M | 37°C 1D | 37°C 1W | 37°C 1M | 50°C 1D | 50°C 1W | 50°C 1M | |
| 16 | 12,800 | 12,800 | 12,800 | 12,800 | 3,200 | 3,200 | 12,800 | 51,200 | 12,800 | 12,800 | 12,800 | 3,200 | 0 |
| 18 | 50 | 200 | 50 | 50 | 0 | 50 | 50 | 50 | 50 | 50 | 0 | 50 | 0 |
| 31 | 50 | 3,200 | 50 | 200 | 200 | 200 | 200 | 800 | 800 | 200 | 200 | 200 | 0 |
| 39 | 0 | 200 | 0 | 0 | 0 | 0 | 0 | 0 | 0 | 0 | 0 | 0 | 0 |
| 5 | 0 | 50 | 0 | 0 | 0 | 0 | 0 | 50 | 0 | 0 | 0 | 0 | 0 |

B. L2-PBNA

| HPV | immune sera raised against lyophilized RG1-VLP stored at | | | | | | | | | | | | PBS |
|---|---|---|---|---|---|---|---|---|---|---|---|---|---|
| | 4°C 1D | 4°C 1W | 4°C 1M | 20°C 1D | 20°C 1W | 20°C 1M | 37°C 1D | 37°C 1W | 37°C 1M | 50°C 1D | 50°C 1W | 50°C 1M | |
| 39 | 50 | 800 | 50 | 200 | 50 | 50 | 50 | 50 | 200 | 50 | 0 | 0 | 0 |
| 5 | 0 | 50 | 0 | 0 | <50 | 0 | 0 | 200 | 0 | 0 | 50 | 50 | 0 |

COMPOSITIONS, METHODS AND USES FOR THERMALLY STABLE MULTI-TARGETED ANTIGENS

PRIORITY

This Continuation Application is a Continuation of application Ser. No. 16/146,686, filed Sep. 28, 2018, allowed, which is a Continuation-in-Part Application that claims priority to U.S. 371 application Ser. No. 15/309,169 filed Nov. 4, 2016, now abandoned, which claims priority to PCT Application No. PCT/US2015/029529 filed May 6, 2015 which claims the benefit of U.S. Provisional Application Ser. No. 61/989,365 filed May 6, 2014. These applications are incorporated herein by reference in their entirety for all purposes.

FIELD

Embodiments of the present invention provide for novel compositions and methods for making and using a thermally stable human papilloma virus (HPV) vaccine or immunogenic formulation or other stabilized multimeric virus vaccine or immunogenic formulation. Certain embodiments concern lyophilizing HPV formulations in the presence or absence of adjuvants. Other embodiments concern lypophilizing HPV capsomere vaccines and other immunogenic agents to increase stability or reduce degradation of the vaccine and/or agents for storage, delivery and use. In yet other embodiments, a single immunogenic formulation can include a thermally stable composition of multiple virus serotypes. Certain embodiments concern lyophilizing multi-targeted antigen complexes in the presence of various agents to increase stability or reduce degradation of antigenic agents prolonging storage stability, delivery and use. In yet other embodiments, a single immunogenic formulation can include a thermally stable composition of a broad-spectrum multi-targeted antigenic composition against multiple pathogens. In some embodiments, a stabilizing formulation can include a hypertonic mixture including one or more disaccharide and one or more volatile salts for lyophilization and prolonged storage of the multi-targeted antigens (e.g. RG1 HPV16VLP) or the like. In yet another embodiment, exposure to elevated temperatures of a stabilized, lyophilized multi-targeted antigen complex disclosed herein can increase cross-reactivity of the complex against multiple pathogens compared to a control when reconstituted and introduced to a subject.

BACKGROUND

Papillomaviruses infect a wide variety of different species of animals including humans. Infection is typically characterized by the induction of benign epithelial and fibroepithelial tumors, or warts at the site of infection. Each species of vertebrate is infected by a species-specific set of papillomaviruses, including several different papillomavirus types. For example, more than one hundred different human papillomavirus (HPV) genotypes have been isolated. Papillomaviruses are highly species-specific infective agents. For example, canine and rabbit papillomaviruses cannot induce papillomas in heterologous species such as humans. Neutralizing immunity to infection against one papillomavirus type generally does not confer immunity against another type, even when the types infect a homologous species.

In humans, papillomaviruses can cause genital warts, a prevalent sexually-transmitted condition. HPV types 6 and 11 are most commonly associated with benign genital warts (e.g., condylomata acuminate). Genital warts are very common, and subclinical or unapparent HPV infection is even more common than clinical infection. While most HPV-induced lesions are benign, lesions arising from certain papillomavirus types e.g., HPV-16 and HPV-18, can undergo malignant progression. Moreover, infection by one of the malignancy-associated papillomavirus types is considered to be a significant risk factor in the development of cervical cancer. Cervical cancer is the third most common cancer in women worldwide. Most cervical cancer cases occur in women living in developing countries where availability of vaccines and preventative screenings, such as pap smears are limited. Human Papillomavirus (HPV) is the etiologic agent associated with cervical cancer, and therefore vaccines against HPV would be very beneficial in reducing the disease prevalence in developing countries.

Delivering an effective HPV vaccine or other multi-targeted antigenic complex compositions to developing countries comes with many challenges. Ideally, the cost of a (e.g., HPV) vaccine for developing countries needs to be inexpensive as possible. Additionally, keeping vaccines at a temperature sufficient to maintain the composition and reduce degradation can be difficult when delivering vaccines to remote regions and limited refrigerated space is available for vaccine storage. The recommended temperature ranges for transporting vaccines in refrigeration or cooler temperatures are narrow. If liquid vaccine formulations are exposed to freezing or elevated temperatures, degradation or loss of efficacy can result. Limitations of maintaining a vaccine in refrigerated storage are even more pronounced when delivering the vaccine in a developing country.

HPV-16 is the most common of the HPV genotypes involved in cervical cancer making up about 50% of cervical cancers. Prevalence of HPV-18 ranges from approximately 8-31% of cervical cancers depending on the geographical location. HPV-45 is the third most frequent oncogenic HPV type. Other cancer-related genotypes include HPV-31, HPV-33, HPV-52, HPV-58, HPV-35, HPV-59 and HPV-56. One of the issues involved with the production and use of HPV vaccines has been effective in providing effective storage and transportation of the vaccines where storage conditions can reduce degradation or increase stability of a viral vaccine formulation.

SUMMARY

Embodiments of the present invention provide for novel compositions and methods for making and using a thermally stable human papilloma virus (HPV) formulation or other stabilized multimeric virus formulation. Certain aspects concern partially or fully lyophilizing or freeze-drying HPV formulations in the presence or absence of one or more adjuvants or other immune-stimulating agents. Other embodiments described herein concern lypophilizing HPV capsomere vaccines or freeze-drying HPV capsomeres constructs to increase stability or decrease degradation or disassembly of the vaccines or constructs during storage, transportation, delivery and use.

In some embodiments, lyophilized glassy-state HPV vaccines can be developed using any HPV antigen in combination with an adjuvant. In certain embodiments, HPV-16 and HPV-18 as well as HPV-31, HPV-33, HPV-35, HPV-39, HPV-45, HPV-51, HPV-52, HPV-56, HPV-6, HPV-11, HPV-30, HPV-42, HPV-43, HPV44, HPV-54, HPV-55, and HPV-70 are contemplated of use herein. In other embodiments, lyophilized glassy-state HPV vaccines can be developed using HPV L1 capsomere proteins as an antigen combined with an adjuvant. Adjuvants contemplated herein include, but are not limited to, aluminum hydroxide or aluminum hydroxide with glycopyranoside lipid A (GLA). In some embodiments, an adjuvant can include an aluminum salt including but not limited to, one or more of aluminum hydroxide, aluminum phosphate and aluminum sulfate, or combinations thereof. In other embodiments, the aluminum salt can be in the form of an aluminum hydroxide gel (e.g., ALHYDROGEL). Other adjuvants contemplated herein include, but are not limited to, calcium-based salts including calcium phosphate, muramyl dipeptide, oligodeoxynucleotides containing CpG motifs, bacterial flagellins, saponins such as Quils. ISCOM and QS21, resquimod, MF 59 emulsions, squalene emulsions, cytokines such as IL-2, IL-12 and GMCSF, silica, polynucleotides, toxins, such as cholera toxin, toxoids, such as cholera toxoid, serum proteins, other viral coat proteins, other bacterial-derived preparations, block copolymer adjuvants, such as Hunter's TITERMAX adjuvant (VAXCEL, Inc., Norcross, Ga.); RIBI adjuvants (available from Ribi ImmunoChem Research, Inc., Hamilton, Mont.), liposomes, and microparticles of polymers such as poly-(lactic acid) and poly-(lactic-co-glycolic acid).

In certain aspects of the invention, vaccine formulations can be lyophilized for example, where an L1 pentamer remains intact. In addition, these combinations can reduce detrimental modifications to critical neutralizing epitopes of the L1 pentamer. In other embodiments, HPV vaccines or compositions disclosed herein preserved antibody titer by increasing stability and/or decreasing disassembly or degradation. In other embodiments, the antigen compositions described herein can reduce antibody titer loss at temperatures of about 40° C. to about 50° C. to about 60° C. degrees for up to several weeks to months making it possible to store and transport vaccine compositions at an increased temperature for a longer duration. It is anticipated that these principles can be applied to other vaccine formulations, including vaccines formulated with virus-like particles, vaccine formulations containing live, attenuated viruses and vaccines containing protein antigens can all benefit from the compositions and methods disclosed herein.

In other embodiments, vaccine compositions of the instant invention can be used to vaccinate subjects in order to reduce consequences of a viral infection or potentially prevent infection and side effects of a viral infection. For example, compositions of HPV 16 L1 capsomere proteins in combination with adjuvants can be lyophilized and transported to remote areas for distribution and administration to subjects in need. In other embodiments, vaccine formulations described herein can be used alone or in combination with other agents used to prevent HPV infections in a subject (e.g., GARDASIL and CERVARIX).

In other embodiments, vaccine or immunogenic compositions disclosed herein can contain multiple types of HPV L1 capsomeres that can be used to immunize or vaccinate subjects in need thereof. In accordance with these embodiments, compositions of mixtures of HPV 16 L1 capsomeres, HPV 18 LI capsomeres, HPV31 capsomeres and/or HPV 45 capsomeres can be co-lyophilized and transported to remote areas for distribution and immunization of subjects in need. In certain embodiments, various combinations of any HPV L1 capsomeres can be combined with adjuvants and co-lyophilized and transported to remote areas for distribution and immunization of subjects in need.

In other embodiments, vaccine or immunogenic compositions disclosed herein can contain multimeric compositions of HPV16 L1, HPV18 L1, HPV 31 L1, and HPV45 L1 capsomeres, for example. In accordance with these embodiments, immunogenic compositions disclosed herein can also contain particulate adjuvants such as aluminum or aluminum salt adjuvants, for example aluminum hydroxide or aluminum hydroxide with glycopyranoside lipid A (GLA), as well as glass-forming agents, such as trehalose and/or sucrose. In some embodiments, these immunogenic compositions can be co-lyophilized, stored and/or transported to remote areas where they can be reconstituted with no loss of multimeric structure or immunogenicity.

Certain embodiments provide for novel compositions and methods for a thermally stable broad-spectrum multi-targeted antigen formulation. Some aspects concern partially or fully lyophilizing or freeze-drying the broad-spectrum multi-targeted antigen formulation in the presence of a hypotonic mixture. Other embodiments described herein concern lyophilizing broad-spectrum multi-targeted antigen constructs (e.g., RG1 HPV16VLPs) to increase stability or decrease degradation or disassembly of the constructs during storage, transportation and delivery resulting in a reduction of product loss and reduction of loss of efficacy.

In some embodiments, broad spectrum multi-targeted antigens can be lyophilized and dried to create powdered formulations. In certain embodiments, constructs can include RG1 HPV16VLPs or similar (U.S. Pat. No. 9,149, 503 is incorporated herein in its entirety for all purposes). In other embodiments, multi-targeted antigen complexes can be lyophilized and dried to create a powdered formulation subjected to elevated temperatures (e.g., 40-60° C.) then reconstituted to enhance an immune response in a subject to the targets represented by the multi-targeted antigen and to enhance cross-reactivity.

In certain embodiments, compositions disclosed herein include, but are not limited to, one or more volatile salts. In accordance with these embodiments, one or more volatile salts can include, but are not limited to, one or more of ammonium acetate, ammonium formate, ammonium carbonate, ammonium bicarbonate, triethylammonium acetate, triethylammonium formate, triethylammonium carbonate, trimethylamine acetate trimethylamine formate, trimethylamine carbonate, pyridinal acetate and pyridinal formate, or combinations thereof.

In other embodiments, formulations of use herein can include one or more non-reducing disaccharides including, but not limited to, trehalose, sucrose and lactose, and optionally, additional glass-forming agents. Glass-forming agents can include, but are not limited to, hydroxyethyl starch, glycine, glycine and mannitol, cyclodextrin, and polyvinyl pyrrolidone (povidone) or combinations thereof.

In some embodiments, formulations of use herein can include a multi-targeted antigen (e.g., VLP assembled from an HPV L1 protein), one or more disaccharide and one or more volatile salt or volatile salt buffer. In accordance with these embodiments, a multi-targeted antigen can be a complex made up of antigens derived from several pathogens (e.g. immunogenic epitopes), a non-reducing disaccharide can include one or more of trehalose, sucrose, lactose, or the like and one or more volatile salts can include one or more of ammonium acetate, ammonium formate, ammonium carbonate, ammonium bicarbonate, triethylammonium acetate, or the like. In certain embodiments, a stabilizing formulation of use to prolong shelf life of a multi-targeted antigen, such as RG1 HPV16VLPs or similar constructs or other multi-faceted antigen complexes can include a hypertonic mixture including trehalose and ammonium acetate.

In certain aspects of the instant disclosure, immunogenic formulations of broad-spectrum multi-targeted antigen formulations can be lyophilized for example, where the broad-spectrum construct remains intact. In addition, these combinations can reduce detrimental modifications to critical neutralizing epitopes of an assembled antigen. In other embodiments, broad-spectrum multi-targeted antigen compositions can preserve antibody titer by increasing stability and/or decreasing disassembly or degradation. In other embodiments, multi-targeted antigen compositions described herein can be stabilized to reduce antibody titer loss when stored at temperatures of about 40° C. to about 50° C. to about 60° C. degrees for up to several weeks to several months making it possible to store and transport without product loss for a longer duration. In certain embodiments, immunogenic compositions of multi-targeted antigens, (e.g., RG1 HPV16VLPs) or the like can be frozen on precooled shelves of a lyophilizer and dried under vacuum creating an essentially dry powder formulation. In other embodiments, these constructs can be combined with trehalose and ammonium acetate lyophilized and dried to prolong shelf-life of the active agents.

In yet other embodiments, these stored formulations can be stored at elevated temperatures (at about 40 to about 60° C.) and subsequently reconstituted for use against multiple pathogens. In certain embodiments, the multi-targeted antigen can be stored at elevated temperatures (at about 40 to about 60° C.) for a few hours, to one day, a week or month or more prior to reconstitution to enhance cross reactivity of the multi-targeted antigen complex.

In other embodiments, vaccine or immunogenic compositions disclosed herein can contain broad-spectrum constructs. In accordance with these embodiments, immunogenic compositions disclosed herein can also contain particulate adjuvants such as aluminum or aluminum salt adjuvants, for example aluminum hydroxide or aluminum hydroxide with glycopyranoside lipid A (GLA), as well as disaccharide agents, such as trehalose and/or sucrose. In some embodiments, these immunogenic compositions can be co-lyophilized, stored and/or transported to remote areas where they can be reconstituted with no loss of multimeric structure or immunogenicity.

BRIEF DESCRIPTION OF THE FIGURES

The following drawings form part of the instant specification and are included to further demonstrate certain aspects of particular embodiments herein. The embodiments may be better understood by reference to one or more of these drawings in combination with the detailed description presented herein.

FIGS. 1A-1C are photographic representations of electron microscope images of certain embodiments presented herein, before lyophilization (A), immediately after lyophilization and reconstitution (B), and after storage in the lyophilized state and reconstituted (C).

FIG. 2 represents an exemplary histogram plot of Stern-Volmer constants for time 0 vaccine formulations of certain embodiments presented herein.

FIGS. 3A and 3B are graphical representations of HPV 16 L1 capsomere reactivity to V5 (A) and L 1(B) antibodies measured using absorbance at 450 nm, according to one embodiment of the present disclosure.

FIG. 4 represents histogram plots of particle size and concentration of HPV vaccines under various storage conditions, according to certain embodiments herein.

FIGS. 5A and 5B represent graphic illustrations of anti-HPV-16 antibodies (A) and neutralizing antibodies (B) after one (solid circles) and two (open circles) vaccine injections for protein (P), protein+alum (PA), protein+alum+GLA (PAG), GARDASIL, and CERVARIX vaccines.

FIGS. 6A and 6B represent a graphic illustration of time 0 and incubated vaccines using anti-HPV-16 antibodies (A) and neutralizing antibodies (B) after one (solid circles) and two (open circles) vaccine injections for protein (P), protein+alum (PA), protein+alum+GLA (PAG), GARDASIL, and CERVARIX vaccines.

FIGS. 7A and 7B represent graphic illustrations of dose response curves for antibody neutralization studies (A) and antibody incubation study in mice (B) for certain vaccine compositions according to embodiments disclosed herein.

FIGS. 8A and 8B are photographic representations of electron microscope transmissions of certain embodiments presented herein, before lyophilization (A), and after lyophilization and reconstitution (B) of HPV16 L1 capsomeres.

FIGS. 9A and 9B are photographic representations of electron microscope transmissions of certain embodiments presented herein, before lyophilization (A), and after lyophilization and reconstitution (B) of HPV18 L1 capsomeres.

FIGS. 10A and 10B are photographic representations of electron microscope transmissions of certain embodiments presented herein, before lyophilization (A), and after lyophilization and reconstitution (B) of HPV31 L1 capsomeres.

FIGS. 11A and 11B are photographic representations of electron microscope transmissions of certain embodiments presented herein, before lyophilization (A), and after lyophilization and reconstitution (B) of HPV45 L1 capsomeres.

FIG. 12 is a photographic representation of an electron microscope transmission of an embodiment presented herein, after lyophilization and reconstitution of a tetravalent formulation containing HPV16 L1, HPV18 L1, HPV31 L1, and HPV45 L1 capsomeres.

FIGS. 13A-13C are photographic representations of SDS Page and Western Blot analysis of certain embodiments presented herein, before lyophilization (A), and after lyophilization and reconstitution (B) of HPV16 L1, HPV18 L1, HPV31 L1, and HPV45 L1 capsomeres, and (C) before lyophilization ("PRE") and after lyophilization and reconstitution ("POST") of a tetravalent formulation containing HPV16 L1, HPV18 L1, HPV31 L1, and HPV45 L1 capsomeres.

FIG. 14 represents a table reflecting exemplary data where titer of a construct of various embodiments disclosed herein was measured at indicated temperatures over time.

FIGS. 15A and 15B represents some data obtained from an exemplary neutralization assay to detect neutralization data against HPV16 as well as some cross neutralization data against other antigens of certain embodiments disclosed herein.

FIG. 16 represents a histogram plot of a mouse model testing stimulation of T cell responses after immunization with a broad-spectrum HPV complex stored in exemplary compositions at various temperatures and times when the mice are exposed to various agents including positive and negative controls.

FIG. 17 represents an image of an exemplary scanning electron micrograph of RGI-HPV VLPs demonstrating intact VLPs in certain embodiments disclosed herein.

DEFINITIONS

In order to facilitate an understanding of the invention, the following definitions are provided.

As used herein, "a" or "an" may mean one or more than one of an item.

As used herein, "about" may mean up to and including plus or minus five percent, for example, about 100 may mean 95 and up to 105.

Capsid protein: the structural protein of a virus, e.g., enveloped, or non-enveloped, which constitutes the capsid structure. Generally, there are several capsid proteins which are often described by whether they are the predominant (major) constituent or lesser (minor) constituent of capsid structure.

Conformational antibody: refers to an antibody that specifically binds an epitope expressed as a correctly-folded L1 or L2 protein but not on denatured L1 or L2 protein.

Capsomere: refers to a structure that makes up the larger viral capsid structure that is generally a pentamer of one type of capsid proteins. In the case of HPV, a native capsomere comprises a pentamer of L1 capsid proteins that may be associated with one L2 capsid protein.

"Capsid" as used herein refers to the structural portion of a virus, e.g., HPV that is comprised of capsomeres. In the case of HPV, the viral capsid is comprised of 72 capsomeres.

"Chimeric protein" as used herein refers to a protein created when two or more genes that normally code for two separate proteins recombine, either naturally or as the result of human intervention, to code for a protein that is a combination of all or part of each of those two proteins.

"Multi-targeted antigen" as used herein refers to an antigen complex where the antigen can be derived from bacteria, viruses, fungi, or segments, peptides, epitopes derived thereof. For example, as used herein a multi-targeted antigen can be a single complex capable of eliciting multiple protective immunogenic responses at the same time, for example, simultaneously.

DETAILED DESCRIPTIONS

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well known methods or components have not been included in the description.

In certain embodiments, compositions, methods and uses for stabilizing HPV vaccine formulations are disclosed. A formulation or application of a formulation that can stabilize viral vaccines from for example, from degradation or dissolution of a viral structure is disclosed. In certain embodiments, compositions disclosed herein can be used to reduce loss of titer of lyophilized HPV formulations. In certain embodiments, compositions disclosed herein can concern a combination of two or more agents (e.g., adjuvant or adjuvant-like agent) provided to an HPV vaccine formulation where the formulation is then lyophilized.

In some embodiments, vaccine formulations can be lyophilized in the presence of glass-forming excipients, and sufficient liquid can be removed during lyophilization that the dried or essentially dried vaccine formulation or immunogenic composition exhibits a glass transition temperature that is higher than the anticipated storage temperature. For example, the anticipated storage temperature may be room temperature.

In certain embodiments, one or more agents provided to a vaccine or immunogenic formulation disclosed herein can include, but is not limited to, one or more aluminum-salt adjuvants, one or more buffer systems containing one or more one volatile salts, one or more one glass-forming agents, one or more immunologically-related co-stimulatory agents and one or more multimeric protein antigens. In certain aspects, a formulation can be combined to create a liquid vaccine or immunogenic formulation. In other aspects, an immunogenic or vaccine formulation can be frozen to create a frozen immunogenic or vaccine formulation. In yet other aspects, the vaccine formulation or immunogenic formulation can be lyophilized to create a dried or essentially dried vaccine or immunogenic composition. In yet other embodiments, the virus compositions disclosed herein can go through a classification step in the presence of one or more adjuvants. Certain embodiments disclosed herein concern incubation of lyophilized multi-targeted antigen complexes exposed for prolonged periods at elevated temperatures to enhance immune response to the multiple targets that make up the multi-targeted antigen and induce enhanced cross-reactivity to various types or serotypes of pathogenic organisms such as viruses, bacteria, fungi or the similar (e.g, flaviviruses, alphaviruses etc.). In one exemplary embodiment, a complex contemplated in formulations and methods disclosed herein can include a RG1 HPV-VLP or similar.

In some embodiments, a multimeric viral protein complex as part of a vaccine or immunogenic composition can include one or more capsomeres formed from proteins derived from a viral capsid. For example, a multimeric viral protein can include a pentamer assembled from LI proteins of the human papilloma virus. In some embodiments, a multimeric viral protein is an HPV 16 L1 capsomere. In other embodiments, a multimeric viral protein can include capsomeres of HPV18 L1 protein, HPV31 L1 protein or HPV45 L1 protein, alone or in combination with HPV 16 L1. In other embodiments, a multimeric viral protein is another HPV complex such as a virus-like particle (VLP) or other viral complex with similar characteristics to a capsomere wherein the glassy excipients disclosed herein stabilize the viral complex when stored or transported at increased temperatures avoiding the need for long-term refrigeration.

In other embodiments, vaccine or immunogenic compositions disclosed herein can contain multimeric compositions of HPV16 L1, HPV18 L1, HPV 31 L1, and HPV45 L1 capsomeres, for example. In accordance with these embodiments, immunogenic compositions disclosed herein can also contain particulate adjuvants. In certain embodiments, particulate adjuvants can be aluminum or aluminum salt adjuvants, for example aluminum hydroxide or aluminum hydroxide with glycopyranoside lipid A (GLA). In other embodiments, these compositions can include glass-forming agents. Glass forming agents can include but are not limited to, trehalose, sucrose, raffinose, ficoll, dextran, sucrose, maltotriose, lactose, mannitol, hydroxyethyl starch, glycine, cyclodextrin, and polyvinyl pyrrolidone (povidone).

In some embodiments, these immunogenic compositions can be co-lyophilized, stored and/or transported to remote areas where they can be reconstituted with no loss of multimeric structure or immunogenicity.

In some embodiments, the aluminum salt adjuvant of the vaccine composition can include one or more of aluminum hydroxide, aluminum phosphate and aluminum sulfate, or combinations thereof. In other embodiments, the aluminum salt can be in the form of an aluminum hydroxide gel (e.g., ALHYDROGEL) or other consistency.

In certain embodiments, a buffer of use in compositions disclosed herein can include, but is not limited to, one or more volatile salts. In accordance with these embodiments, one or more volatile salts can include, but are not limited to, one or more of ammonium acetate, ammonium formate, ammonium carbonate, ammonium bicarbonate, triethylammonium acetate, triethylammonium formate, triethylammonium carbonate, trimethylamine acetate trimethylamine formate, trimethylamine carbonate, pyridinal acetate and pyridinal formate, or combinations thereof.

In other embodiments, a glass-forming agent (e.g., when freeze-dried the compositions forms a glass-like consistency instead of crystals) disclosed herein can include one or more of trehalose, sucrose, ficoll, dextran, sucrose, maltotriose, lactose, mannitol, hydroxyethyl starch, glycine, cyclodextrin, and povidone, or combinations thereof. In some embodiments, the glass-forming agent in a weight-to-volume (w/v) concentration of from about 1% to about 20%, or about 5% to about 15% in a liquid vaccine formulation prior to lyophilization. In other embodiments, the glass-forming agent can be trehalose present in a concentration of from about 8% to about 20% w/v in the liquid vaccine formulation prior to lyophilization. In another embodiment, the glass-forming agent can be trehalose at a concentration of about 9.5% w/v in the liquid vaccine formulation or immunogenic composition prior to lyophilization. Glass-forming agents that can be used in accordance with the various embodiments of the present disclosure can include, but are not limited to, trehalose, sucrose, ficoll, dextran, sucrose, maltotriose, lactose, mannitol, hydroxyethyl starch, glycine, cyclodextrin, polyvinyl pyrrolidone, and the like.

In some embodiments, compositions disclosed herein can include both a buffer composed of volatile salts and a glass forming agent at concentrations that are hypertonic prior to lyophilization, but that as a result of buffer volatilization during the lyophilization process become isotonic upon reconstitution.

In some embodiments, a co-stimulatory agent of a vaccine or immunogenic composition disclosed herein can include one or more of lipid A, lipid A derivatives, monophosphoryl lipid A, chemical analogues of monophosphoryl Lipid A, CpG containing oligonucleotides, TLR-4 agonists, flagellin, flagellins derived from gram negative bacteria, TLR-5 agonists, fragments of flagellins capable of binding to TLR-5 receptors, saponins, analogues of saponins, QS-21, purified saponin fractions, ISCOMS and saponin combinations with sterols and lipids, or combinations thereof. In some embodiments, the co-stimulatory agent can be about 0.05 mg/mL Glycopyranoside lipid A (GLA).

In some embodiments, a vaccine composition can be formulated to include about 0.1 mg/mL HPV 16 L1 capsomere, about 0.5 mg aluminum hydroxide gel (e.g., ALHYDROGEL), about 0.05 mg/mL Glycopyranoside lipid A (GLA) in 54 mM histidine HCl (pH about 7.1), and about 9.5 w/v % trehalose.

In some embodiments, stability of vaccine or immunogenic compositions disclosed herein can be enhanced by the addition of nonionic surfactants. In accordance with these embodiments, surfactants can be added to vaccine or immunogenic formulations at concentrations ranging from approximately 0.1 times the critical micelle concentration of the surfactant in the vaccine composition, to approximately 20 times the critical micelle concentration of the surfactant in the vaccine composition before, during or after lyophilization of the composition. Suitable nonionic surfactants include, but are not limited to, polysorbates such as Tween 20, Tween 40, Tween 60 and Tween 80, poloxamers for example Polaxamer 188 and Poloxamer 407, Poloxamer 235, Poloxamer 335, Brij, alkylphenol hydroxypolyethylene surfactants such as Triton X100, Triton X114 and Triton X405, and Oligoethylene glycol monoalkyl ethers such as Genapol.

In certain embodiments, compositions, methods and uses for stabilizing multi-targeted antigen formulations are disclosed. A formulation or application of a formulation that can stabilize antigenic vaccine complexes from; for example, from degradation or dissolution of a viral structure is contemplated. In certain embodiments, compositions disclosed herein can be used to reduce loss of titer of lyophilized multi-targeted antigen formulations (e.g., HPV). In other embodiments, compositions disclosed herein can concern a combination of two or more agents (e.g., adjuvant or adjuvant-like agent) provided to a multi-targeted antigenic formulation where the formulation is then lyophilized.

In certain embodiments, a multi-targeted antigen contemplated herein can include antigens derived from two or more pathogenic organisms. In accordance with these embodiments, a multi-targeted antigen can include antigens from multiple species or multiple pathogens complexed to for a multi-targeted antigen. For example, a chimeric viral complex, live attenuated virus complexes, multi-peptide cytomegalovirus (CMV)-modified vaccinia Ankara (MVA) vaccine, Plasmodium falciparum multiple-antigen peptide vaccines, PnuBioVax (PBV multi-antigen, serotype-independent prophylactic vaccine against *S. pneumoniae* disease, ALVAC(2), melanoma multi-antigen therapeutic vaccine, bacterial backed complexes (e.g. salmonella, MVA constructs), flavivirus antigenic complexes, alphavirus antigenic complexes are contemplated herein.

In some embodiments, vaccine formulations can be lyophilized in the presence of one or more disaccharide and one or more volatile salt and sufficient liquid can be removed during lyophilization that the dried or essentially dried vaccine formulation or immunogenic composition is stabilized from degradation. In other embodiments, these complexes can be stored for one day, one week, one month or more. One anticipated storage temperature of lyophilized complexes disclosed herein can be room temperature or higher (e.g. about 30° C. to about 60° C.).

Embodiments of the present invention provide for novel compositions and methods for a thermally stable broad-spectrum multi-targeted antigen formulation. Certain aspects concern partially or fully lyophilizing or freeze-drying the broad-spectrum multi-targeted antigen formulation in the presence of a hypotonic mixture. Other embodiments described herein concern lyophilizing broad-spectrum constructs (e.g. RG1 HPV16VLPs) to increase stability or decrease degradation or disassembly of the constructs during storage, transportation, delivery resulting in a reduction of product loss and reduction of loss of efficacy.

In some embodiments, broad spectrum multi-targeted antigens are lyophilized and dried to create powdered formulations. In certain embodiments, constructs can include RG1-VLPs, RG1 HPV16VLPs or similar (U.S. Pat. No. 9,149,503 is incorporated herein in its entirety for all purposes).

In certain embodiments, compositions disclosed herein include, but are not limited to, one or more volatile salts. In accordance with these embodiments, one or more volatile salts can include, but are not limited to, one or more of ammonium acetate, ammonium formate, ammonium carbonate, ammonium bicarbonate, triethylammonium acetate, triethylammonium formate, triethylammonium carbonate, trimethylamine acetate trimethylamine formate, trimethylamine carbonate, pyridinal acetate and pyridinal formate, or combinations thereof.

In other embodiments, formulations of use herein can include one or more non-reducing disaccharides including, but not limited to, trehalose, sucrose and lactose, and additional glass forming agents, as necessary, including, but not limited to, hydroxyethyl starch, glycine, glycine and mannitol, cyclodextrin, and polyvinyl pyrrolidone (povidone) or combinations thereof.

In certain aspects of the instant disclosure, immunogenic formulations of broad-spectrum multi-targeted antigenic formulations, for example, can be lyophilized where the broad-spectrum construct remains intact. In addition, these combinations can reduce detrimental modifications to critical neutralizing epitopes of an assembled multi-targeted complex. In other embodiments, broad-spectrum multi-targeted construct compositions disclosed herein preserve antibody titer by increasing stability and/or decreasing disassembly or degradation. In certain embodiments, antigen compositions described herein can be stabilized to reduce antibody titer loss by lyophilization in buffers disclosed herein. In other embodiments, lyophilized multi-targeted antigenic complexes can be stored at elevated temperatures of about 40° C. to about 50° C. to about 60° C. degrees for up to several weeks to several months making it possible to store and transport these compositions at an increased temperature for a longer duration. In certain embodiments, immunogenic compositions of multi-targeted antigens or the like can be frozen on precooled shelves of a lyophilizer and dried under vacuum creating an essentially dry powder formulation. In other embodiments, multi-targeted antigens or the like formulations including trehalose and ammonium acetate can be lyophilized and dried to prolong shelf-life of the active agents for storage and transport or enhance immunogenicity.

"Multimeric" Protein

Generally, as the complexity of vaccine compositions increases, long term stability decreases, especially at elevated temperatures. In some cases, vaccines compositions comprising multiple subunits (e.g., multimeric) can have greater complexity than vaccine compositions that are made of single proteins. For example, vaccine compositions comprising antigens based on multiple capsomere subunits are generally more complex and more resistant to forming stable vaccine compositions. In some cases, embedding a capsomere within glassy matrices formed during lyophilization can enhance thermal stability of the vaccine composition by stabilizing the tertiary structure of the capsomeres.

In some embodiments, thermal stability of tertiary structure of a viral complex can be assessed by any method known in the art. In other embodiments, thermal stability of tertiary structure of a viral complex can be assessed using various methods including, but not limited to, front face fluorescence. For example, front face fluorescence can be used to examine tertiary structure of HPV 16 L1 capsomeres. In certain embodiments, front face fluorescence can use Acrylamide quenching to assess the tryptophan environment in each vaccine formulation, and a Stern-Volmer constant can be calculated based on the fluorescence. A high Stern-Volmer constant is generally indicative of greater tertiary instability, which allows tryptophan residues to be more easily quenched. For example, a lower Stern-Volmer constant is generally indicative of less tertiary instability (i.e., a more native protein structure), which reduces tryptophan quenching. Thus, these comparisons can be made on a complex to assess stability of the complex at a given temperature in compositions described herein.

In other embodiments, a non-reducing disaccharide disclosed herein can include one or more of trehalose, sucrose, lactose, or combinations thereof. In some embodiments, the disaccharide concentration in a weight-to-volume (w/v) can be from about 1% to about 20%, or about 5% to about 15% (w/v) in a liquid vaccine formulation prior to lyophilization. In other embodiments, the glass-forming agent can be trehalose present in a concentration of from about 8% to about 20% w/v in the liquid vaccine formulation prior to lyophilization. In another embodiment, the glass-forming agent can be trehalose at a concentration of about 10% w/v in the liquid vaccine formulation or immunogenic composition prior to lyophilization.

In some embodiments, compositions disclosed herein can include a hypertonic buffer composed of volatile salts and a disaccharide agent at various concentrations (1.0% to 20% (w/v)) prior to lyophilization. In other embodiments, a broad-spectrum multi-targeted antigenic construct disclosed herein included in a stabilizing composition for lyophilization or other purpose can be from about 0.01 mg/mL to about 5.0 mg/mL, or about 0.01 mg/mL to about 3.0 mg/mL; or about 0.01 mg/mL to about 2.0 mg/mL; or about 0.05 mg/mL to about 1.5 mg/mL. In some embodiments, a multi-targeted antigen construct can be formulated in a stabilizing composition for lyophilization or other purpose can be from about 0.05 mg/mL to about 2.0 mg/mL.

In some embodiments, stability of vaccine or immunogenic compositions disclosed herein can be enhanced by the addition of nonionic surfactants. In accordance with these embodiments, surfactants can be added to vaccine or immunogenic formulations at concentrations ranging from approximately 0.1 times the critical micelle concentration of the surfactant in the vaccine composition, to approximately 20 times the critical micelle concentration of the surfactant in the vaccine composition before, during or after lyophilization of the composition. Suitable nonionic surfactants include, but are not limited to, polysorbates such as Tween 20, Tween 40, Tween 60 and Tween 80, poloxamers for example Poloxamer 188 and Polaxamer 407, Poloxamer 235, Poloxamer 335, Brij, alkylphenol hydroxypolyethylene surfactants such as Triton X100, Triton X114 and Triton X405, and oligoethylene glycol monoalkyl ethers such as Genapol.

In some embodiments, thermal stability of tertiary structure of a broad-spectrum multi-targeted complex can be assessed by any method known in the art. In other embodiments, thermal stability of tertiary structure of broad-spectrum multi-targeted complexes can be assessed using various methods including, but not limited to, front face fluorescence. For example, front face fluorescence can be used to examine tertiary structures of certain complexes. In certain embodiments, front face fluorescence can use acrylamide quenching to assess the tryptophan environment in each vaccine formulation, and a Stern-Volmer constant can be calculated based on the fluorescence. A high Stern-Volmer constant is generally indicative of greater tertiary instability, which allows tryptophan residues to be more easily quenched. For example, a lower Stern-Volmer constant is generally indicative of less tertiary instability (i.e., a more native protein structure), which reduces tryptophan quenching. Thus, these comparisons can be made on a complex to assess stability of the complex at a given temperature in compositions described herein.

VLPs and Capsomeres

Virus-like particles or VLPs: the capsid-like structures that result upon expression and assembly of a papillomavirus L 1 DNA sequence alone or in combination with an L2 DNA sequence. VLPs are morphologically and antigenically similar to authentic virions. VLPs may be produced in vivo, in suitable host cells or may form spontaneously upon purification of recombinant L1 and/or L2 proteins. Additionally, they may be produced using capsid proteins L1 and L2, fragments or mutated forms thereof, e.g., L1 or L2 proteins that have been modified by the addition, substitution or deletion of one or more amino acids. L1 and L2 mutants that fall within the scope of the present invention are those that upon expression present at least one native PV conformational epitope. Methods to assemble VLPs are known in the art, as would be readily appreciated and is understood by one of ordinary skilled based on the present disclosure.

Correctly-folded L1 or L2 protein: L1 or L2 protein, fragment thereof, or mutated form thereof, (either monomeric, in the form of small oligomers (dimers-tetramers) or capsomeres), which, upon expression, assumes a conformational structure that presents one or more conformational HPV L1 or L2 epitopes present on native viral capsids or VLPs and is suitable for assembly into VLPs. In the present invention, a correctly folded HPV L1 or L2 protein will present one or more HPV L1 or L2 conformational epitopes.

A conformational LI or L2 HPV epitope: generally refers to an epitope expressed on the surface of correctly-folded L1 or L2 protein which is also expressed by an L1 or L2 protein or fragment, or mutated form thereof, which is also expressed by an L1 or L2 protein of a corresponding wild-type, infectious HPV. It is well accepted by those skilled in the art that the presentation of conformational epitopes is essential to the efficacy (both as prophylactic and diagnostic agents) of HPV L I or L2 protein immunogens.

A conformational neutralizing L1 or L2 HPV epitope: generally refers to an epitope expressed on the surface of correctly-folded L1 protein, fragment or mutated form thereof, which is also expressed by an L1 or L2 protein of a corresponding wild-type, infectious HPV, and which elicits neutralizing antibodies. It is well accepted by those skilled in the art that the presentation of conformational neutralizing epitopes is essential to the efficacy (both as prophylactic and diagnostic agents) of HPV L1 or L2 protein immunogens.

Embodiments herein provide for compositions and methods for stabilizing vaccine or immunogenic formulations and prolong stability during storage for HPV vaccines or immunogenic compositions. In some embodiments, an HPV chimeric protein of compositions disclosed herein can include a papillomavirus L2 capsid polypeptide having a papillomavirus capsid protein L1-binding domain and a second polypeptide comprising at least one immunogenic epitope, wherein the polypeptides are fused at their amino or carboxy terminal ends. The papillomavirus L2 capsid polypeptide can include the full-length papillomavirus L2 capsid protein as well as truncated versions of the L2 protein containing an L1 capsid protein binding region. Additionally or alternatively, the present disclosure provides a chimeric protein comprising a papillomavirus L1 protein linked by at least one amino acid to a second polypeptide comprising at least one immunogenic epitope. The papillomavirus L1 capsid polypeptide can include the full-length papillomavirus L1 capsid protein as well as truncated versions of the L1 protein.

Certain embodiments can include vaccine formulations of capsomeres, including but not limited to, truncated L1 with or without L2 viral proteins. In some embodiments, capsomeres include truncated L 1 proteins. Truncated proteins contemplated herein can include those having one or more amino acid residues deleted from the carboxy terminus of the L1 protein, or one or more amino acid residues deleted from the amino terminus of the L 1 protein, or one or more amino acid residues deleted from an internal region of the protein. In accordance with these embodiments, a capsomere vaccine formulation or immunogenic composition can include L1 proteins truncated at the carboxy terminus.

Immunogenic epitopes are those that confer protective immunity, allowing a mammal or other animal to resist (delayed onset of symptoms or reduced severity of symptoms), as the result of its exposure to the antigen of a pathogen, disease or death that otherwise follows contact with the pathogen. Protective immunity can be achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes that result in sIGA production by B lymphocytes on mucosa-lined tissues of the body. "Humoral immunity" is the result of IgG antibodies and IgM antibodies in serum. "Cellular immunity" can be achieved through cytotoxic T lymphocytes or through delayed-type hypersensitivity that involves macrophages and T lymphocytes, as well as other mechanisms involving T cells without a requirement for antibodies. The primary result of protective immunity is the destruction of the pathogen or inhibition of its ability to replicate itself.

Embodiments of the present disclosure can include a complex including chimeric proteins and further include a papillomavirus L1 polypeptide, protein or fragment thereof, or substantially identical protein or fragments. Papillomavirus L1 polypeptides of the present invention include polypeptides that retain their ability to bind to papillomavirus L2 polypeptides of the present invention. The complexes disclosed herein can include L1 capsid protein fragments that upon expression present conformational, neutralizing epitopes. These fragments can include full length papillomavirus L1 capsid proteins as well as internal, carboxy- and amino-terminal deletions, and proteins having specific cysteine mutations that prevent assembly into VLPs. The deletion may range in size from 1 to about 100 amino acids, preferably 1 to 50 amino acids, and more preferably from about 1 to 25 amino acids. It is essential that the deletion still allow for the expression of a capsid protein, e.g., HPV L1 protein, that when expressed in fused or non-fused form presents at least one conformational, neutralizing epitope.

Complexes disclosed herein can be in the form of a capsomere. Capsomeres of the present invention will generally have a stoichiometry of about one chimeric protein of the present invention to about five papillomavirus L1 capsid proteins, although capsomeres of greater or lesser stoichiometry are also contemplated.

In another embodiment, the capsomeres of the present invention can be assembled into a VLP. In this embodiment, assembly can be performed using methods known in the art. The present invention includes methods to assemble a VLP using capsomeres of the present invention at acidic to physiological pH. Most preferred are methods to assemble VLPs using capsomeres of the present invention at physiologic pH. In the case of polypeptide sequences which are less than 100% identical to a reference sequence, the non-identical positions are preferably, but not necessarily, conservative substitutions for the reference sequence.

Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Similar minor variations may also include amino acid deletions or insertions, or both. Guidance in determining which amino acid residues may be substituted, inserted, or deleted without abolishing biological or immunological activity may be found using computer programs well known in the art.

Viral proteins of the present disclosure may be derived from any papillomaviruses, including human papillomavirus. For example, HPV L1 and L2 DNA sequences exhibit significant homology to L 1 s and L2s of different serotypes of HPV. Therefore, HPV L1 or L2 nucleic acid sequences can be obtained, as would be understood by one of ordinary skill in the art based on the present disclosure.

In some embodiments, the HPV L1 or L2 DNA disclosed herein derived from an HPV which is involved in cancer or condylomata acuminata, e.g., HPV-16, HPV-18, HPV-31, HPV-33, HPV-35, HPV-39, HPV-45, HPV-51, HPV-52, and HPV-56 are involved in cancer, and HPV-6, HPV-11, HPV-30, HPV-42, HPV-43, HPV44, HPV-54, HPV-55, and HPV-70, are involved in warts. However, the subject capsid proteins may be produced using any HPV L1 DNA.

Proteins and capsomeres disclosed herein can be produced in a variety of ways, including production and/or recovery of natural proteins, production and/or recovery of recombinant proteins, and/or chemical synthesis of the proteins. The proteins and polypeptides disclosed herein can be expressed in a prokaryotic microbial host, e.g., bacteria such as *E. coli*, that can be cultured under conditions that favor the production of capsid proteins. This will largely depend upon the selected host system and regulatory sequences contained in the vector, e.g., whether expression of the capsid protein requires induction. Proteins and polypeptides of the present disclosure may also be expressed in any host cell that provides for the expression of recoverable yields of the polypeptides in appropriate conformation. Suitable host systems for expression of recombinant proteins are well known and include, by way of example, bacteria, mammalian cells, yeast, and insect cells. One expression system of use to produce complexes disclosed herein can include *E. coli* expression system used in the Examples, as this system provides for high capsomere yields. However, HPV L1 and L2 proteins, as well as other viral capsid proteins, can be produced in other systems. For example, yeast and baculovirus-infected insect cell cultures can be used.

Suitable vectors for cloning and expressing polypeptides of the present invention are well known in the art and commercially available. Further, suitable regulatory sequences for achieving cloning and expression, e.g., promoters, polyadenylation sequences, enhancers and selectable markers are also well known. The selection of appropriate sequences for obtaining recoverable protein yields is routine to one skilled in the art.

Other embodiments can include polynucleotides that encode chimeric proteins and complexes/capsomeres. Accordingly, any nucleic acid sequence, which encodes the amino acid sequence of chimeric proteins and complexes/capsomeres, can be used to generate recombinant molecules that express chimeric proteins and complexes/capsomeres. It will be appreciated by those skilled in the art based on the present disclosure that as a result of the degeneracy of the genetic code, a multitude of nucleotide sequences encoding chimeric proteins and complexes/capsomeres of the present disclosure, some bearing minimal homology to the nucleotide sequences of any known and naturally occurring gene, may be produced. Thus, the disclosure contemplates each and every possible variation of nucleotide sequence that could be made by selecting combinations based on possible codon choices. These combinations are made in accordance with the standard triplet genetic code as applied to the nucleotide sequence of naturally occurring chimeric proteins and complexes/capsomeres of the present disclosure, and all such variations are to be considered as being disclosed.

Chimeric proteins and capsomeres have application in both prophylactic and therapeutic vaccines and diagnostics. The suitability of the chimeric proteins and capsomeres produced for use as vaccines or as diagnostic agents can be confirmed by reaction with antibodies or monoclonal antibodies which react or recognize conformational epitopes present on the intact vision and based on their ability to elicit the production of neutralizing antiserum. Suitable assays for determining whether neutralizing antibodies are produced are known to those skilled in the art based on the present disclosure. This is an essential characteristic of HPV capsid proteins or other viral capsid proteins, which are to be used in HPV or other viral vaccines. In this manner, it can be verified whether the polypeptides of the present disclosure will elicit the production of anti-HPV neutralizing antibodies. Thus, other expression vectors and expression systems can be tested for use in the present disclosure.

Certain embodiments disclosed herein concern using adjuvants to increase immunogenicity of viral complex compositions or formulations for vaccines. Adjuvants are typically substances that generally enhance the immune response of a patient to a specific antigen. Suitable adjuvants include, but are not limited to, other bacterial cell wall components, aluminum based salts, calcium based salts, silica, polynucleotides, toxins, such as cholera toxin, toxoids, such as cholera toxoid, serum proteins, other viral coat proteins, other bacterial-derived preparations, block copolymer adjuvants, such as Hunter's TITERMAX adjuvant (VAXCEL, Inc., Norcross, Ga.); RIBI adjuvants (available from Ribi ImmunoChem Research, Inc., Hamilton, Mont.) and saponins and their derivatives, such as QUIL A (available from Superfos Biosector A/S, Denmark). Carriers are typically compounds that increase half-life of a composition or agent in a subject. Suitable carriers include, but are not limited to, polymeric controlled release formulations, biodegradable implants, liposomes, bacteria, viruses, oils, esters and glycols.

Certain embodiments of the present application include polypeptides that elicit an immune response to an HPV antigen in a subject. An elicited immune response may be either prophylactic, preventing later infection by the specific viral type targeted, or may be therapeutic, reducing the severity of disease. An immune response includes a humoral, e.g., antibody, response to that antigen and/or a cell-mediated response to that antigen. Methods to measure an immune response are known to those skilled in the art. If one or both types of immune response are present, they may protect a subject from any disease caused by an agent, for example, by the agent from which the viral complex was derived. In accordance with the present disclosure, the ability of an immunogenic composition to protect or treat a subject in need thereof from disease can refer to the ability of a capsomere or chimeric protein of the present disclosure to treat, ameliorate and/or prevent disease or infection caused by the agent or cross reactive agent, by eliciting an immune response against an antigen derived from the disease-causing agent and contained within a protein or capsomere of the present disclosure. It is to be noted that a subject may be protected by an immunogenic composition disclosed herein even without detection of a humoral or cell-mediated response to the immunogenic composition. Protection or reducing the risk of developing a viral infection can be measured by methods known to those skilled in the art.

In certain aspects, because it is known that more than one HPV type may be associated with an HPV infection, vaccines or immunogenic compositions can include stable HPV capsid proteins derived from more than one type of HPV where the compositions have been lyophilized with glass-forming excipients to increase their stability to non-refrigerated temperatures. For example, HPV 16 and 18 are known to be associated with cervical carcinomas, therefore, a vaccine for cervical neoplasia can include VLPs of HPV 16; of HPV 18; or both HPV 16 and 18. In fact, a variety of neoplasias are known to be associated with PV infections. For example, HPVs 3a and 10 have been associated with flat warts. A number of HPV types have been reported to be associated with epidermodysplasia verruciformis (EV) including HPVs 3a, 5, 8, 9, 10, and 12. HPVs 1, 2, 4, and 7 have been reported to be associated with cutaneous warts and HPVs 6b, 1 1 a, 13, and 16 are associated with lesions of the mucus membranes. Thus, the subject vaccine formulations may comprise a mixture of capsid proteins or fragments derived from different BPV types depending upon the desired protection.

Other embodiments concern pharmaceutical immunogenic compositions for use in reducing the risk of onset or treating a condition caused by a pathogenic virus (e.g., HPV). Any known pharmaceutically acceptable excipient is contemplated herein.

Yet another aspect of the present disclosure is a method to elicit an immune response to a chimeric protein or capsomere of a lyophilized or dehydrated composition (after hydration), comprising administering to the subject a composition disclosed herein. The vaccines will be administered in prophylactically or therapeutically effective amounts. That is, in amounts sufficient to produce a protective immunological response. Generally, the vaccines will be administered in dosages ranging from about 0.1 mg protein to about 20 mg protein, more generally about 0.001 mg to about 1 mg protein. Single or multiple dosages can be administered.

Administration of the subject capsid protein-containing vaccines may be effected by any pharmaceutically acceptable means, e.g., parenterally, locally or systemically, including by way of example, oral, intranasal, intravenous, intramuscular, and topical administration. The manner of administration is affected by factors including the natural route of infection. The dosage administered will depend upon factors including the age, health, weight, kind of concurrent treatment, if any, and nature and type of the particular viral, e.g., human, papillomavirus. The vaccine may be employed in dosage form such as capsules, liquid solutions, suspensions, or elixirs, for oral administration, or sterile liquid formulations such as solutions or suspensions for parenteral or intranasal use.

In yet other embodiments, multi-targeted antigen complexes can be lyophilized and stored in elevated temperatures of about 40° C. to about 60° C. for a pre-determined period of days to months (e.g. 1 day, 1 week, several weeks to a month or more) to enhance immunity when introduced to a subject to a broad range of types or serotypes of pathogenic organisms. For example, enhancing epitope availability or enhancing neutralization effects of a composition as a result of exposure to these elevated temperatures during storage. In certain embodiments, enhanced immunogenicity can occur in simultaneously to the represented antigens of the complex. This aspect of the instant invention is surprising and unexpected as elevated temperatures typically have an adverse effect on immunogenicity of multi-complexed agents. In accordance with these embodiments, exposure to increased temperatures as reference above of a stabilized, lyophilized multi-targeted antigen (e.g. RG1 HPV VLP), of the instant application, can increase cross-reactivity of the reconstituted complex against multiple pathogenic types or serotypes when introduced to a subject. In certain embodiments, a subject contemplated herein can be a human subject or other mammalian subject such as a pet or livestock.

Certain embodiments disclosed herein can include kits of use for storage and transport of one or more multi-targeted antigen construct disclosed herein, one or more container and/or one or more lyophilized multi-targeted antigen construct. In accordance with these embodiments, a kit can include a container having a lyophilized multi-targeted antigen construct in trehalose and ammonium acetate or similar agent as disclosed herein.

EXAMPLES

This disclosure is further illustrated by the following non-limiting examples. All scientific and technical terms have the meanings as understood by one with ordinary skill in the art. The examples which follow illustrate the methods in which the chimeric compositions of the present disclosure may be prepared and used and are not to be construed as limiting the disclosure in sphere or scope. The methods may be adapted to variation in order to produce compositions embraced by this disclosure but not specifically disclosed. Further, variations of the methods to produce the same compositions in somewhat different fashion will be evident to one skilled in the art based on the present disclosure.

Example 1

In certain exemplary methods, it is known that liquid vaccines that contain microparticulate adjuvants such as aluminum hydroxide may be particularly prone to damage resulting from accidental freezing, because of the tendency of these adjuvants to agglomerate during freezing. Limitations of refrigerated storage for vaccines are even more pronounced when delivering vaccines to a developing country or region. Lyophilization can be used to embed vaccine antigens and adjuvants within glassy organic matrices, providing an environment where combination of low molecular mobility and low moisture content assist in minimizing antigen degradation. By utilizing high concentrations of glass-forming excipients and in certain cases rapid freezing rates, agglomeration and ultimate degradation caused by microparticulate adjuvants can be avoided or minimized during the lyophilization process.

Embodiments of the present disclosure can be used to increase stability and/or immunogenicity of vaccine formulations through the use of lyophilization to preserve or stabilize the immunogenic complexes. Lyophilization of various vaccine formulations have been demonstrated to decrease protein degradation by, for example, immobilizing vaccine components in a high viscosity glassy matrix with low water content. In some cases, a high glass transition temperature allows for storage in a glassy state at elevated temperatures without significantly increasing protein degradation. For example, trehalose can be used to stabilize the protein in both the liquid and the solid state and can increase the glass transition temperature. Storage of the vaccine formulations below the glass transition temperature allows for the formulation to be stored in a glassy state.

Lyophilized formulations of the present disclosure generally have low water content and do not absorb water during storage. Low water content can help prevent degradations from occurring. Although vaccine particle sizes can vary, it was found that cooling rate and trehalose concentration are two factors that can affect aluminum adjuvant particle size after lyophilization. However, particle size was found to remain constant after storage and antigen tertiary structure was found to be preserved after lyophilization.

In some embodiments, the immunogenicity of vaccine formulations that have undergone lyophilization can be increased by the addition of adjuvants. For example, aluminum salts such as aluminum hydroxide, can create a humoral (Th2) response, and Toll-like receptor 4 (TLR4) agonists such as glycopyranoside lipid A (GLA), can create a cellular (Th1) response. The addition of agonists such as these can increase antibody titers and increase the rate of seroconversion, even after storage at 40° C.

Vaccine Characterization

In certain exemplary methods, it is desirable to store vaccine formulations below both the protein melting temperature and the lyophilized formulation glass transition temperature. For example, the onset melting temperature of the HPV 16 L1 capsomere was determined to be approximately 60° C. (not shown). The melting temperature of HPV VLPs types 6, 11, 16, and 18 found in GARDISIL are all above this temperature (Shank-Retzlaff 2006). The onset glass transition temperature for lyophilized placebo formulations was found to be 97.2° C.±3.4° C., and when an adjuvant was added (e.g., aluminum salt), the onset glass transition temperature for lyophilized placebo formulations was found to be between 102.6° C.±5.2° C. The addition of protein to these formulations did not significantly affect the glass transition temperature. By storing vaccines below both the protein melting temperature and glass transition temperature, protein will not immediately denature upon storage and the lyophilized vaccines will be stored in a glassy state with extremely low mobility. A storage temperature of 50° C. was chosen to evaluate stability for subsequent experimental evaluation.

Certain exemplary embodiments of the vaccines or immunogenic compositions of the present disclosure were characterized in liquid form before lyophilization, immediately after lyophilization reconstitution, and after storage at 50° C. for 12 weeks in both liquid and lyophilized forms. Vaccines were analyzed for capsomere appearance, for example, front face fluorescence was used for tertiary structure, V5 and L1 assays were used for conformational epitope reactivity, and FlowCAM was used for particle size and concentration.

Figure 1B:
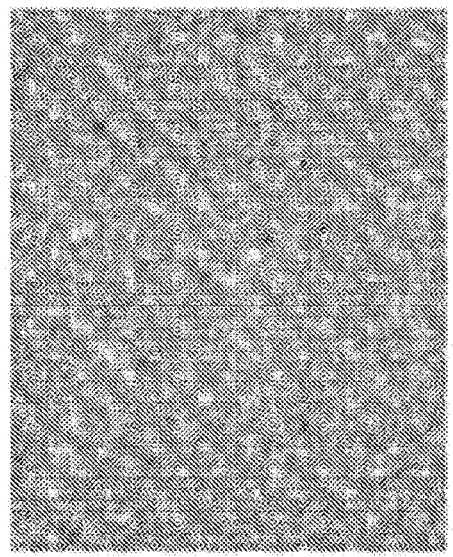
Figure 1C:
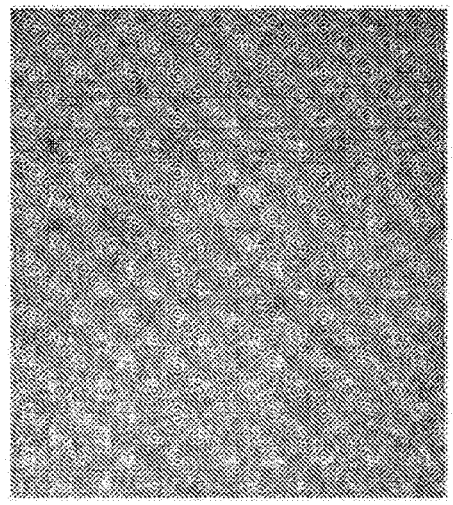

As illustrated in FIGS. 1A-1C, transmission electron microscopy (TEM) was used to visualize HPV 16 L1 capsomeres before lyophilization (A), immediately after lyophilization and reconstitution (B), and after storage in the lyophilized and reconstituted state (C). Before lyophilization, HPV 16 capsomeres are uniformly spherical in nature. After lyophilization and reconstitution, capsomere proteins are similar to their initial state. Additionally, storing the lyophilized vaccine for 12 weeks at 50° C. did not affect capsomere appearance. These data demonstrate that the quaternary structure of HPV 16 L1 capsomeres is preserved after lyophilization. The scale bar represents 100 nm.

Additionally, capsomeres were maintained as a pentamer of L1 proteins during lyophilization as demonstrated by retention of the capsomere peak in size exclusion chromatography. The area under the peak was integrated to be 422, 0, 413, and 415 arbitrary units for liquid HPV 16 L1 capsomere, stored liquid HPV 16 L1 capsomere, lyophilized HPV 16 L1 capsomere, and stored lyophilized HPV 16 L1 capsomere respectively (data not shown). After storage at 50° C. in the liquid state the capsomere protein was completely lost, demonstrating that the instant compositions and methods were capable of preserving/stabilizing the complex as observed by presence of a capsomere peak in the treated conditions.

Example 2

Figure 2:
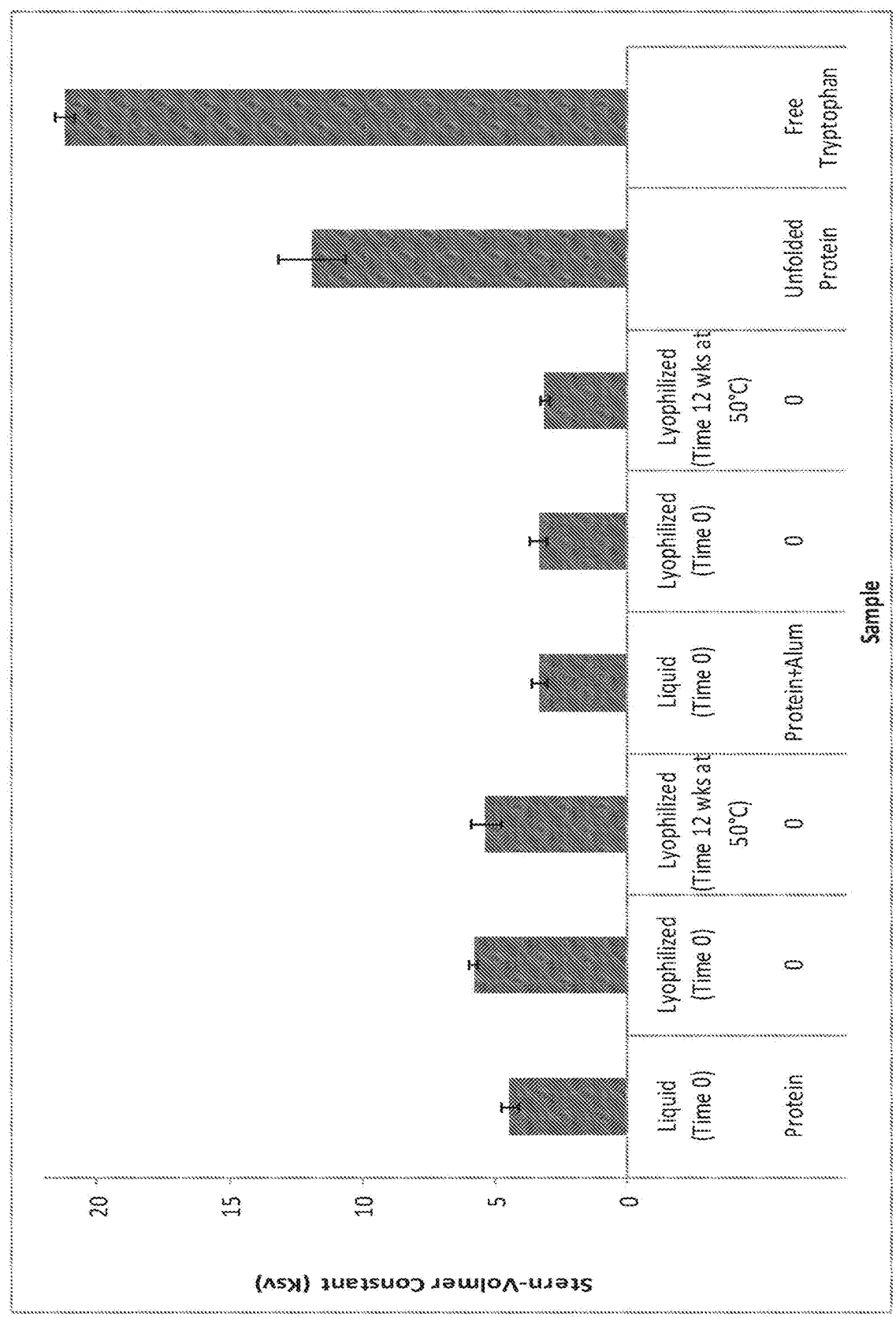

In another exemplary method, to examine the tertiary structure of HPV 16 L1 capsomere proteins, front face fluorescence was used. In one example, the tryptophan environment in each vaccine formulation was assessed, acrylamide quenching was performed, and a Stern-Volmer constant was calculated. A high Stern-Volmer constant is indicative of more unfolding of the protein allowing for tryptophan residues to be more easily quenched, whereas a lower Stern-Volmer constant indicates that the tryptophan residues were more difficult to access, thus indicating a more native-like protein tertiary structure. The Stern-Volmer constant remained constant for the initial liquid state, the reconstituted and lyophilized state, and for the lyophilized incubated and reconstituted state (e.g., after storage), for both protein and protein+alum vaccines, as illustrated in FIG. 2. These data demonstrate that the tertiary structures of the vaccines in these embodiments were retained after lyophilization and storage. The protein+alum vaccines had a slightly lower Stern-Volmer constant which may be due to tryptophan residues adsorbing the aluminum hydroxide adjuvant and therefore being less accessible to acrylamide.

Figure 3A:
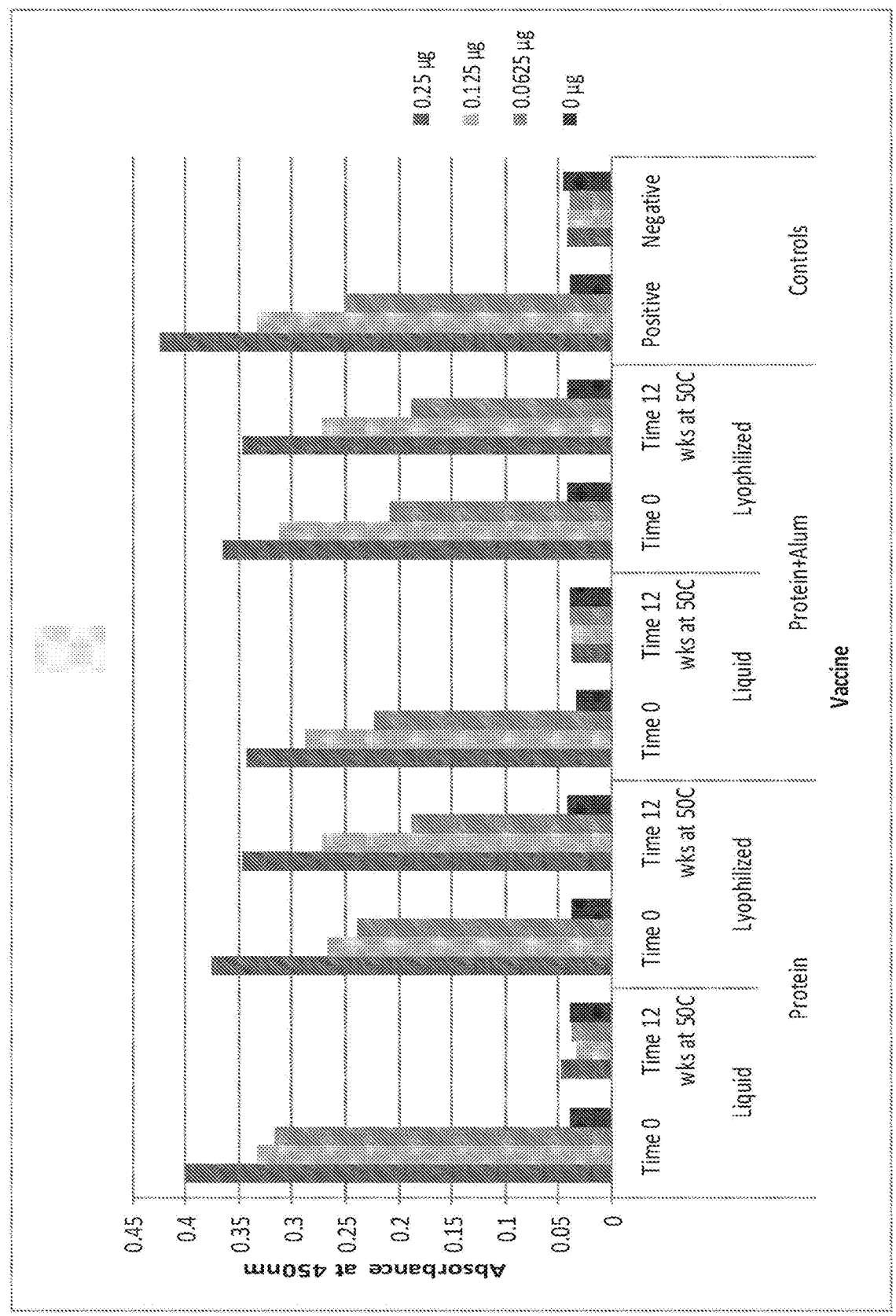
Figure 3B:
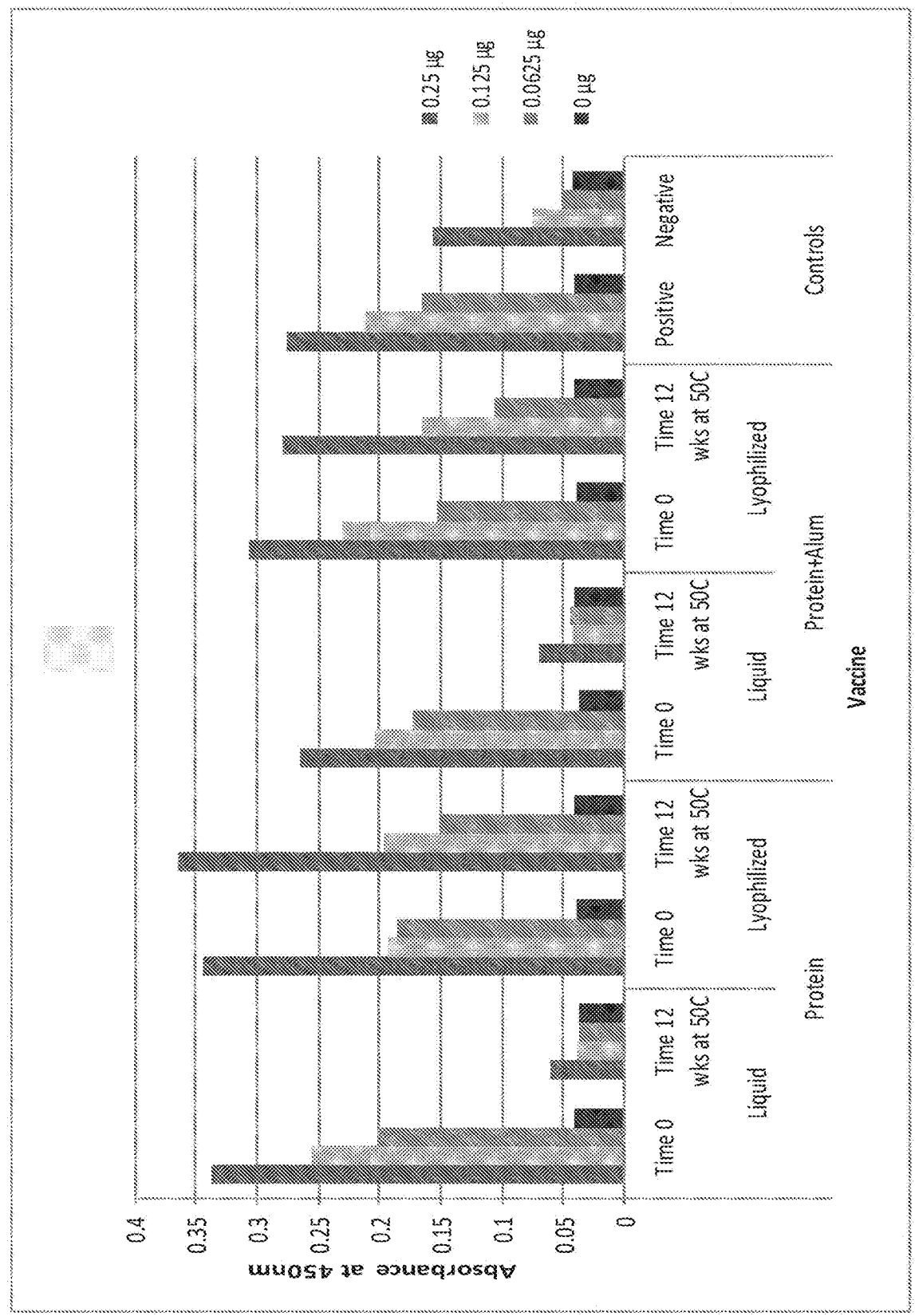
Figure 4:
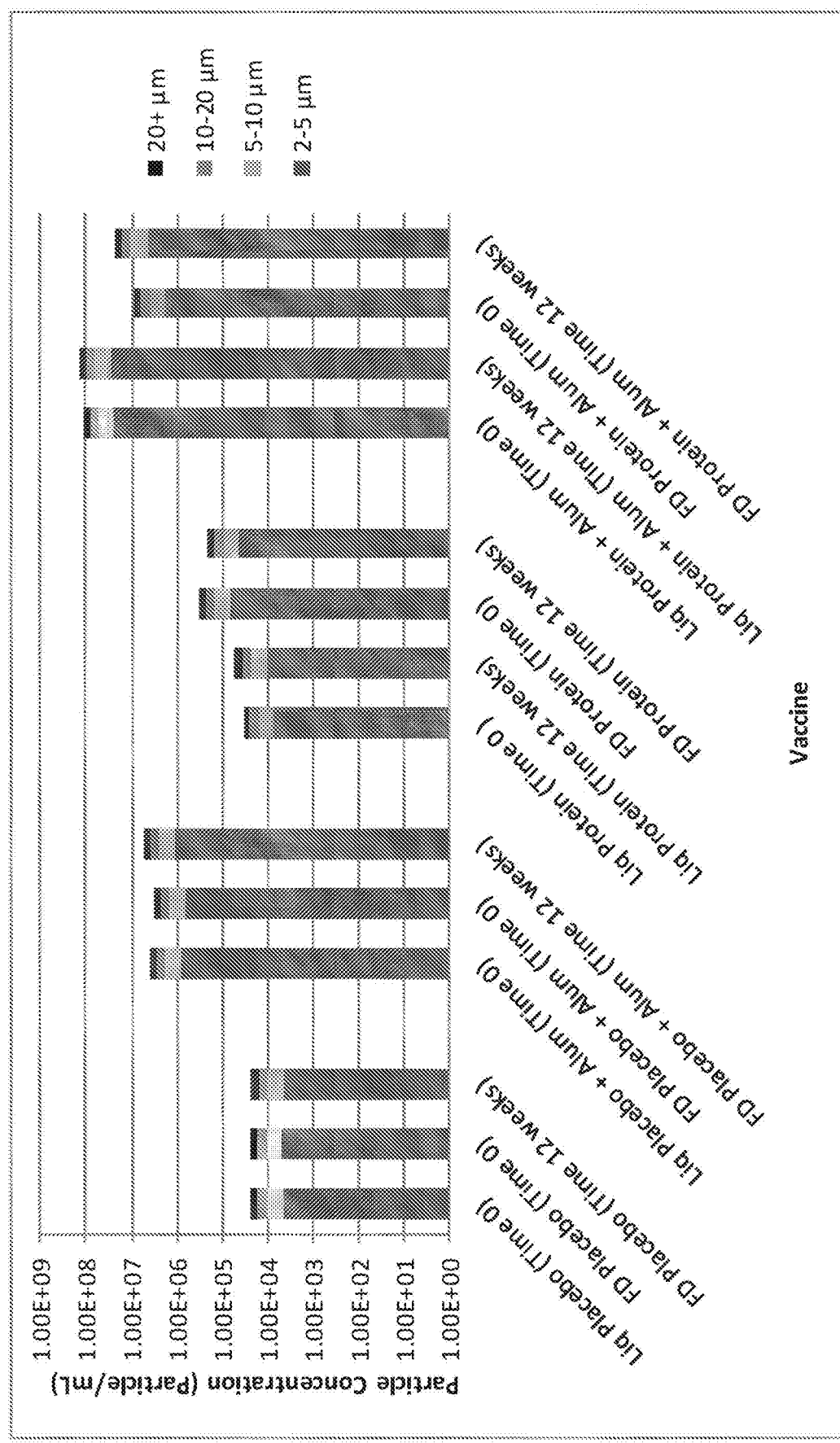

Experiments were also conducted to demonstrate the reactivity of HPV 16 L1 capsomeres to two antibodies, V5 (FIG. 3A) and L1 (FIG. 3B). L1 antibody reactivity was used to monitor the structure of many epitopes of the L1 subunit in the capsomere, and V5 antibody reactivity was used to monitor a conformational neutralizing epitope presented by the pentamer. As demonstrated, reactions with both antibodies were retained during the lyophilization process, as well as after elevated temperature storage in the lyophilized state (FIG. 4). The positive control used for comparison was a fresh sample of the HPV 16 L1 capsomere protein, while the negative control used was a polyomavirus structural protein, VP1, a structural equivalent to L1.

Example 3

Vaccine Immunogenicity

Because HPV 16 L1 capsomere protein was preserved during storage as provided above, immunogenicity of the stored vaccine as compared to the initial vaccine was evaluated. Particle concentrations were assessed prior to testing immunogenicity. As shown in FIG. 4, the concentrations of particles greater than 2 microns (pm) remained fairly constant through lyophilization and storage, with approximately 5×104 particles/mL for placebo groups and protein formulations and 5×106 particles/mL for placebo+alum and protein+alum formulations.

Figure 5A:
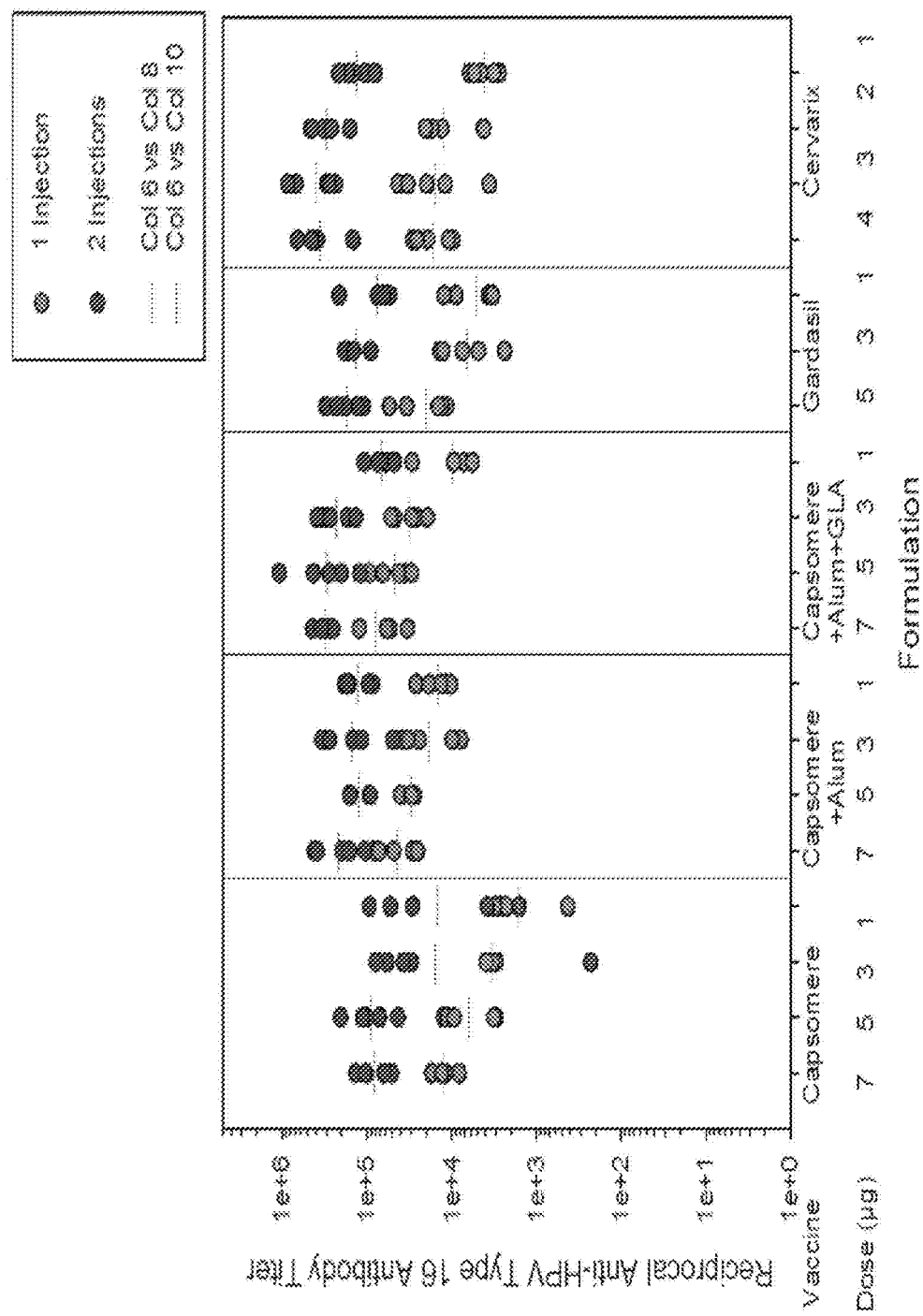
Figure 5B:
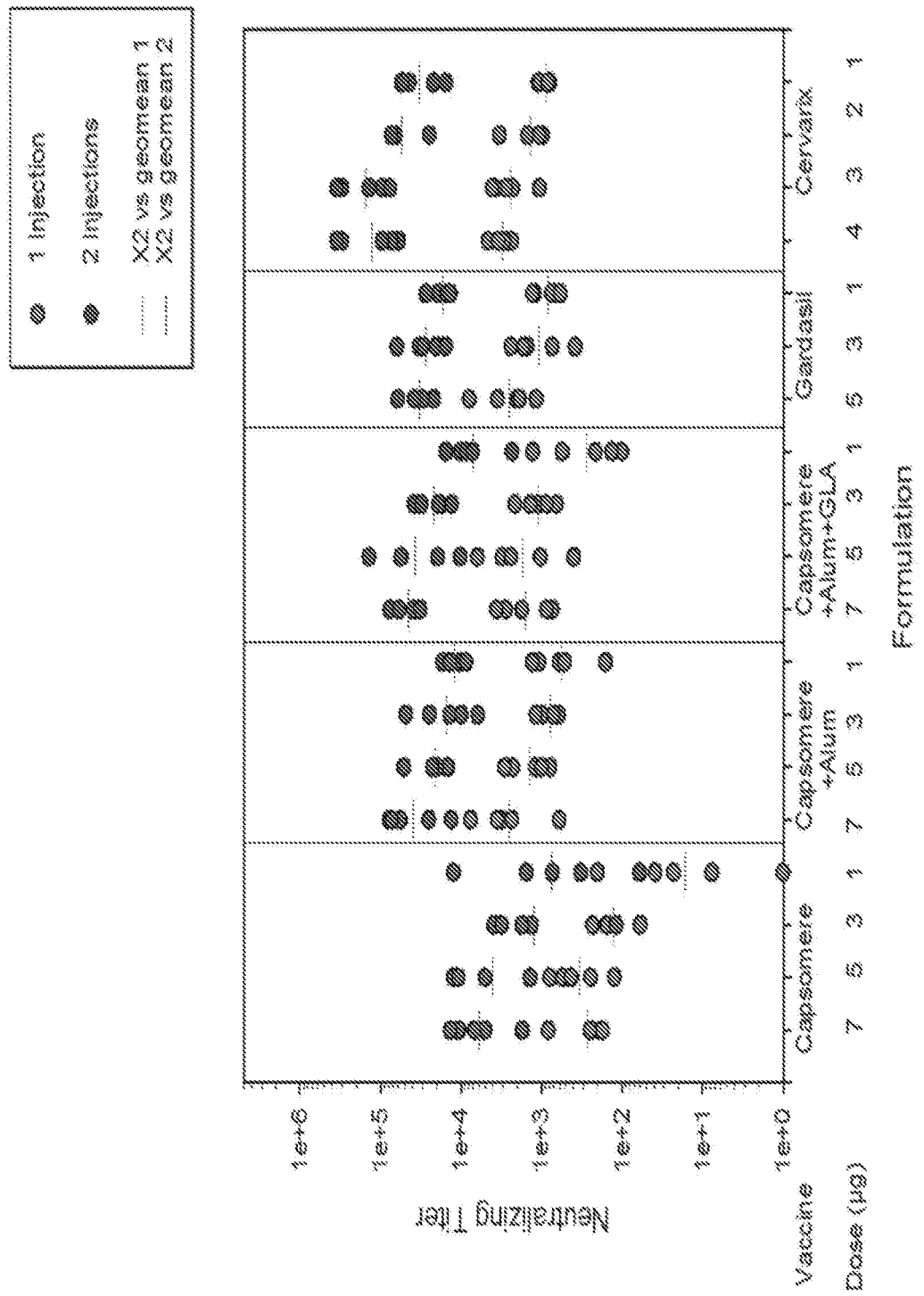

Vaccine immunogenicity was assessed by measuring total anti-HPV 16 L1 capsomere antibody titers (FIG. 5A) as well as neutralizing antibody titers (FIG. 5B). A dose response relationship was demonstrated for lyophilized vaccines (protein (P) and protein+alum (PA)), at doses of 7, 5, 3, and 1 µg/dose, for GARDISIL at doses of 5, 3, and 1 µg/dose, and for CERVARIX at doses of 4, 3, 2, and 1 µg/dose. All of the doses administered were in the linear range based on the murine model used. All doses of formulations containing the adjuvant aluminum hydroxide had significantly ($p<0.05$) greater immune responses than formulations containing only protein after one and two injections, except the 5 µg dose after two injections (p=0.46). The addition of aluminum hydroxide increased the antibody titers one order of magnitude from protein alone. GLA did not significantly increase the antibody titers (p>0.05) after one or two injections. Additionally, lyophilized vaccines containing adjuvants preformed equally as well if not better than commercially available vaccines based on total IgG antibody titers.

Figure 6A:
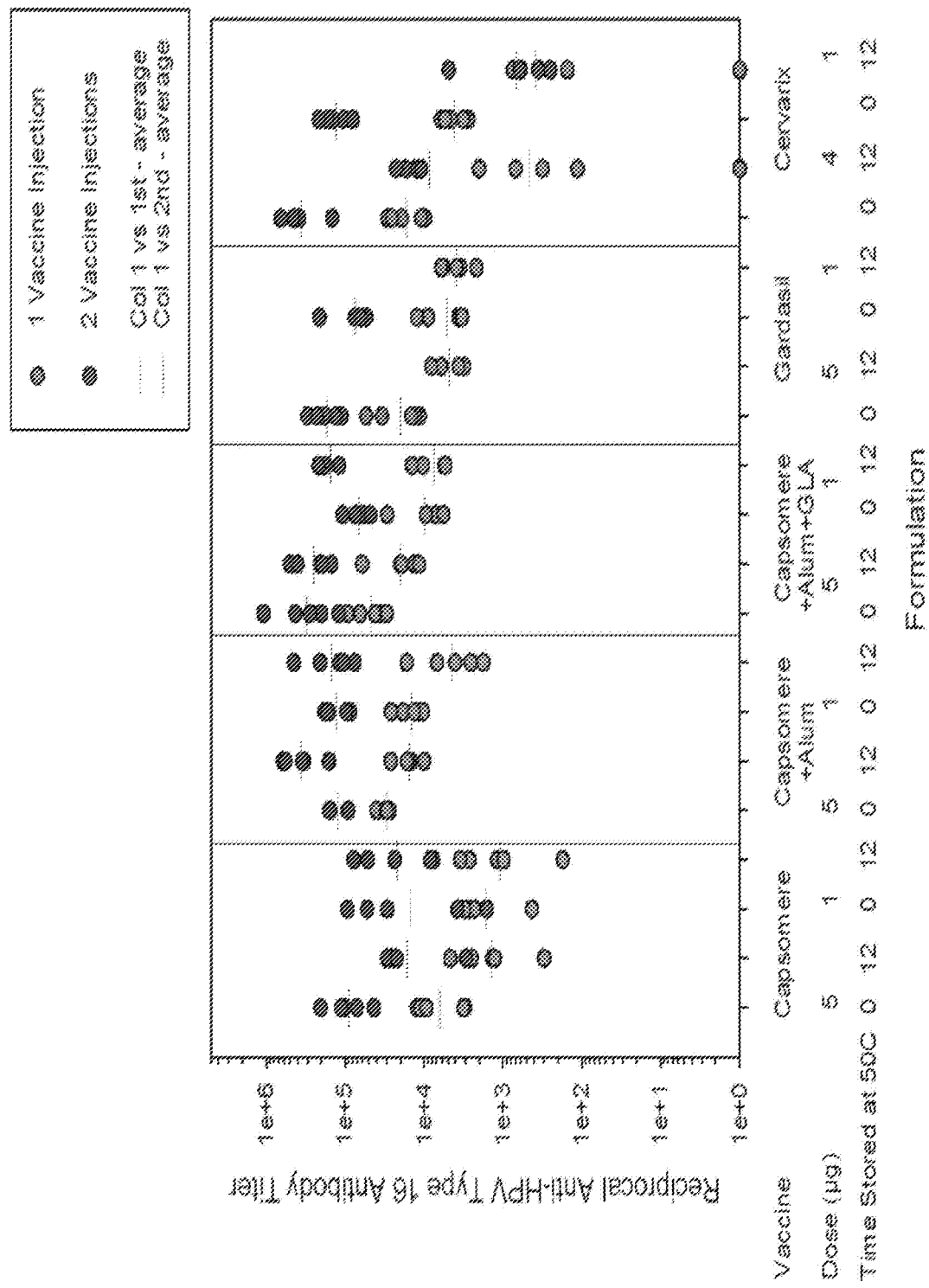
Figure 6B:
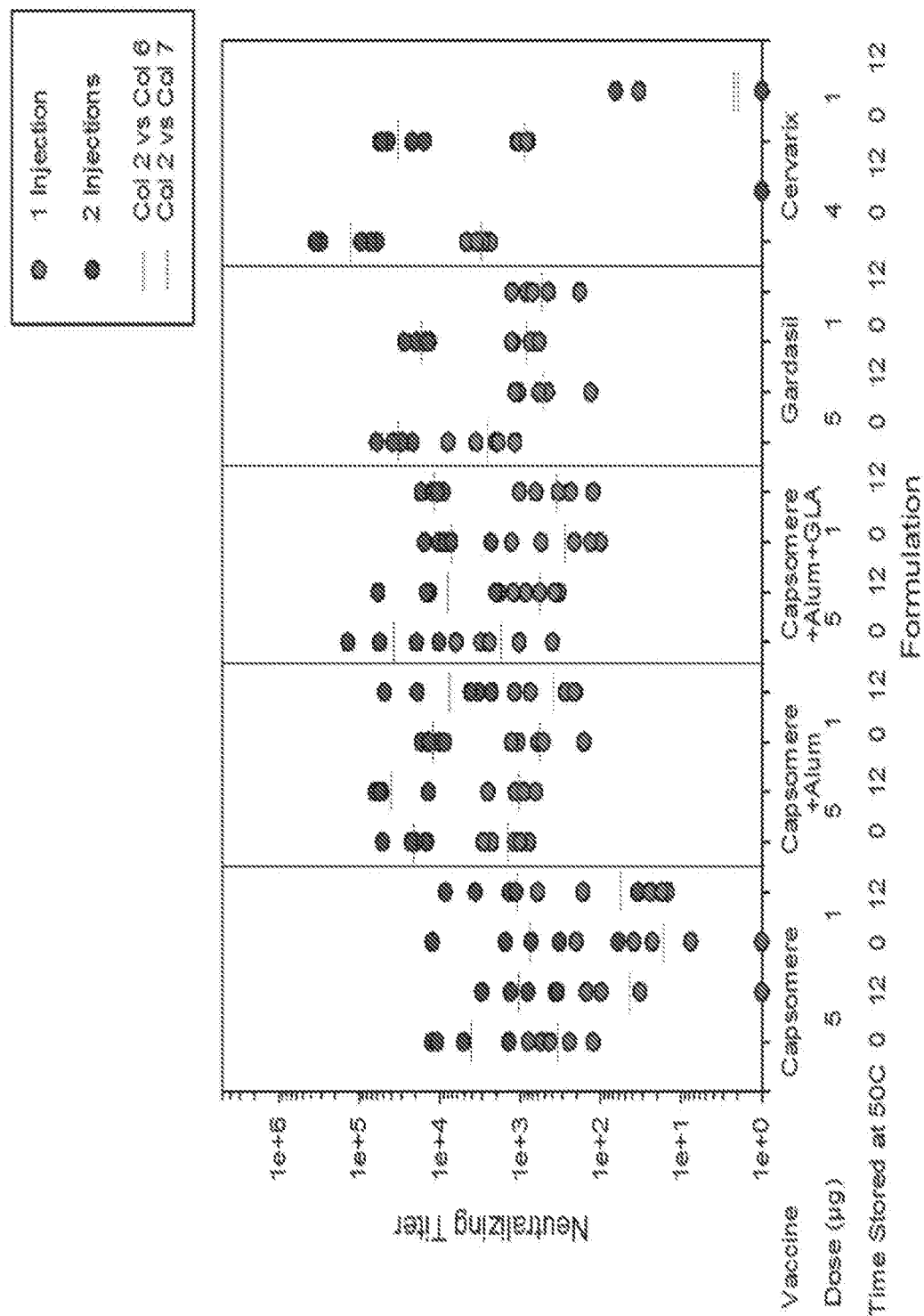

Lyophilized vaccine formulations were incubated at 50° C. for 12 weeks and then injected into mice at 5 and 1 µg/dose since these were found to be in the linear range of the immune response. GARDASIL and CERVARIX were injected at 5 and 1, and 4 and 1 µg/dose, respectively. Due to a limited supply of GARDASIL, only one dose was administered for the incubated vaccines. As illustrated in FIG. 6A, lyophilized vaccines produced anti-HPV 16 L1 capsomere antibody titers similar to their non-incubated counterparts with the exception of the protein only vaccines at a 5 [tg dose after two vaccine injections. Neutralizing antibody titers are illustrated in FIG. 6B. GARDASIL had similar titer values after one injection, but CERVARIX had significantly (p=0.008) decreased titers. The predicted half-life of GARDASIL at 42° C. is a few months; however, these data demonstrate that at a longer incubation time, even at 50° C., high antibody titers were maintained.

Figure 7A:
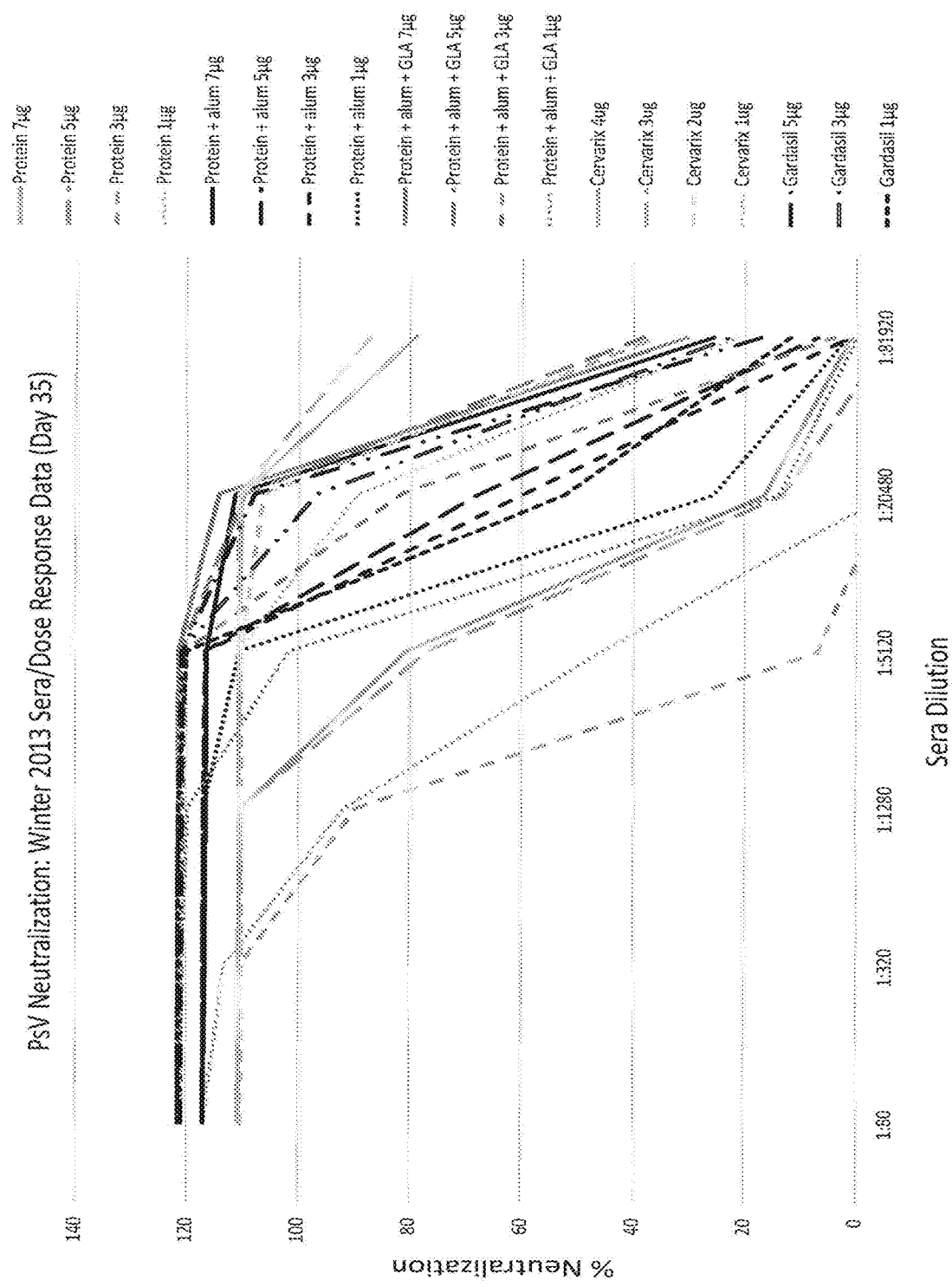
Figure 7B:
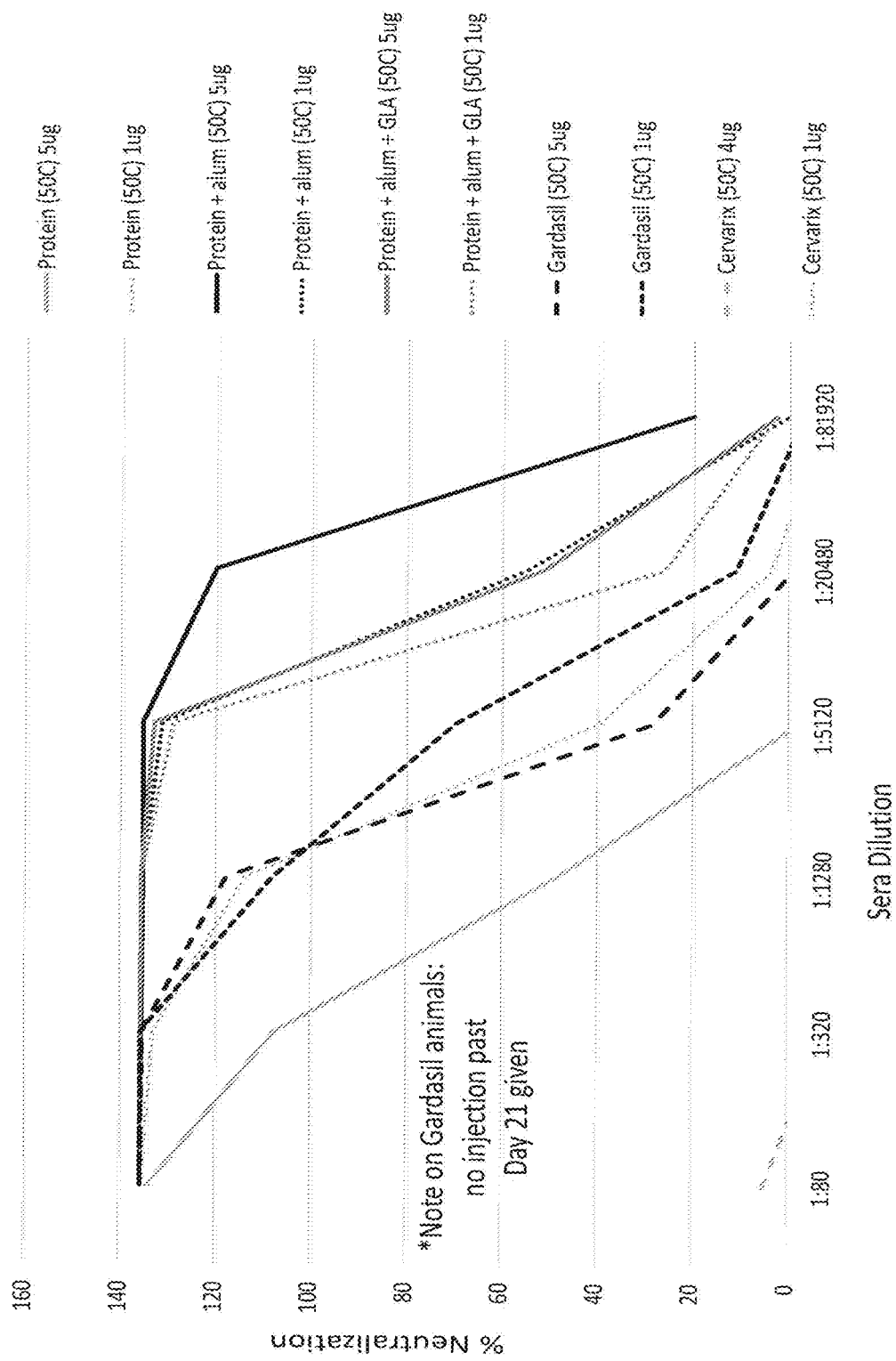

FIGS. 7A and 7B illustrate graphical representations of dose response curves for an antibody neutralization study (A) and an antibody incubation study in mice (B) for various vaccine formulations, according to embodiments of the present disclosure.

Taken together, these data demonstrate that lyophilized HPV 16 L1 capsomere vaccines remained stable and highly immunogenic after an elevated storage temperature of about 50° C. for the 12 weeks tested, stabilizing the formulation for storage, delivery and use. The potentially lower cost of the capsomere protein, in conjunction with the high thermostability of the lyophilized vaccine, makes these preparations excellent candidates for HPV vaccines, for example, for developing countries where access to these types of vaccines is reduced.

Example 4

In another exemplary method, preparation of HPV vaccine formulations, alum-adjuvanted HPV vaccine formulations and alum- and MPLA-adjuvanted HPV vaccine formulations containing capsomeres of HPV16 LI, HPV18 L1, HPV31 L1 or HPV45 L1, as well as tetravalent HPV vaccine formulations containing mixtures of capsomeres of HPV16 L1, and alum- and MPLA-adjuvanted HPV vaccine formulations containing capsomeres of HPV16 LI, HPV18 L1, HPV31 L1 or HPV45 L1 were generated.

In certain examples, aqueous protein solutions were formulated to contain either HPV 16, 18, 31, or 45 capsomeres at a concentration of 0.05 mg/mL. Formulations were prepared in 100 mM histidine buffer at pH 7.1 with 9.5 w/v % trehalose as 1 mL aliquots. a, a-Trehalose dehydrate and L-histidine monohydrochloride monohydrate were purchased from Sigma-Aldrich (St. Louis, Mo.). Each HPV strain was formulated in three ways: (i.) with no adjuvant present, (ii.) with 0.5 mg/mL aluminum from ALHYDROGEL and (iii.) with 0.5 mg/mL aluminum from ALHYDROGEL with 0.05 mg/mL MPLA. ALHYDROGEL adjuvant 2% (also referred to herein as alum) (e.g., E.M. Sergeant Pulp & Chemical Co, Inc., Clifton, N.J.). Synthetic monophosphoryl lipid A (MPLA) a glyclopyranoside lipid An adjuvant; Avanti Polar Lipids, Inc. Alabaster, Ala.

In one example, formulations containing ALHYDROGEL were rotated end-over-end at 8 rpm in 1.5 mL polypropylene microcentrifuge tubes at 4° C. for 1 hour to allow capsomere adsorption onto adjuvant. Additionally, a formulation containing 0.0125 mg/mL of all four HPV capsomere types (16, 18, 31, and 45) was made without adjuvant as a control.

Comparisons of TEM images that were recorded before lyophilization and after lyophilization and reconstitution (FIGS. 8-11) for formulations containing capsomeres of each type alone (HPV16 LI, HPV18 L1, HPV31 L1 or HPV45 L1), as well as tetravalent vaccine formulations containing all four HPV capsomere types (FIG. 12), demonstrated that the pentameric conformation of the HPV capsomere were retained through the lyophilization and reconstitution process.

Western blot analysis of aluminum hydroxide-adjuvanted formulations of vaccines containing HPV16 L1 capsomeres, HPV18 L1 capsomeres, HPV31 L1 capsomeres, or HPV45 L1 capsomeres sampled prior to lyophilization and after lyophilization and reconstitution demonstrated that antigenic epitopes were retained after lyophilization and reconstitution (FIGS. 13A-13C). Furthermore, samples from tetravalent vaccine formulations containing aluminum hydroxide adjuvant also showed retention of antigenic epitopes after lyophilization and subsequent reconstitution, as measured using ELISA assays.

Figure 8A:
Figure 8B:
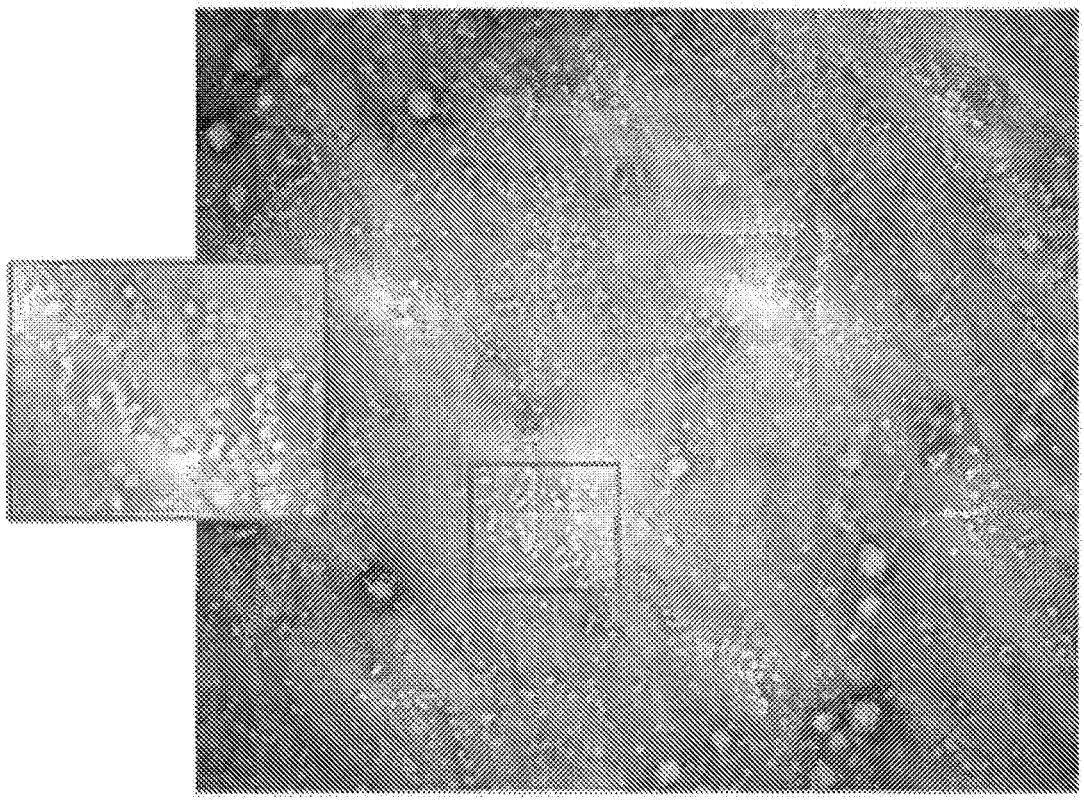

In FIGS. 8A and 8B, TEM images of HPV16 L1 capsomeres were captured before lyophilization (A) and after lyophilization and reconstitution (B).

Figure 9A:
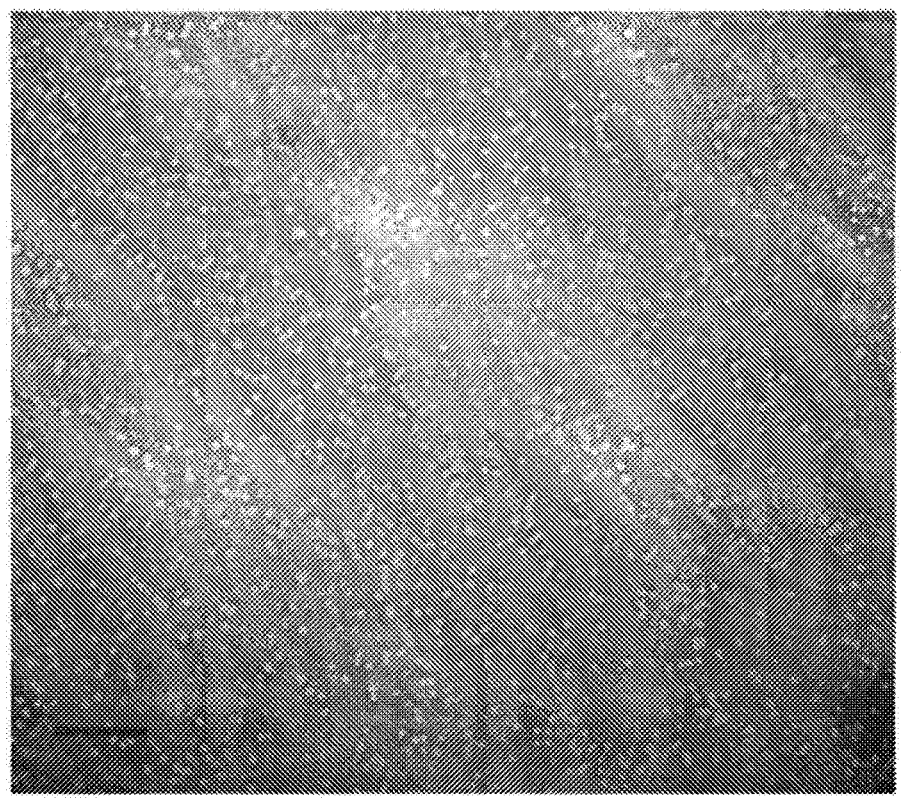
Figure 9B:
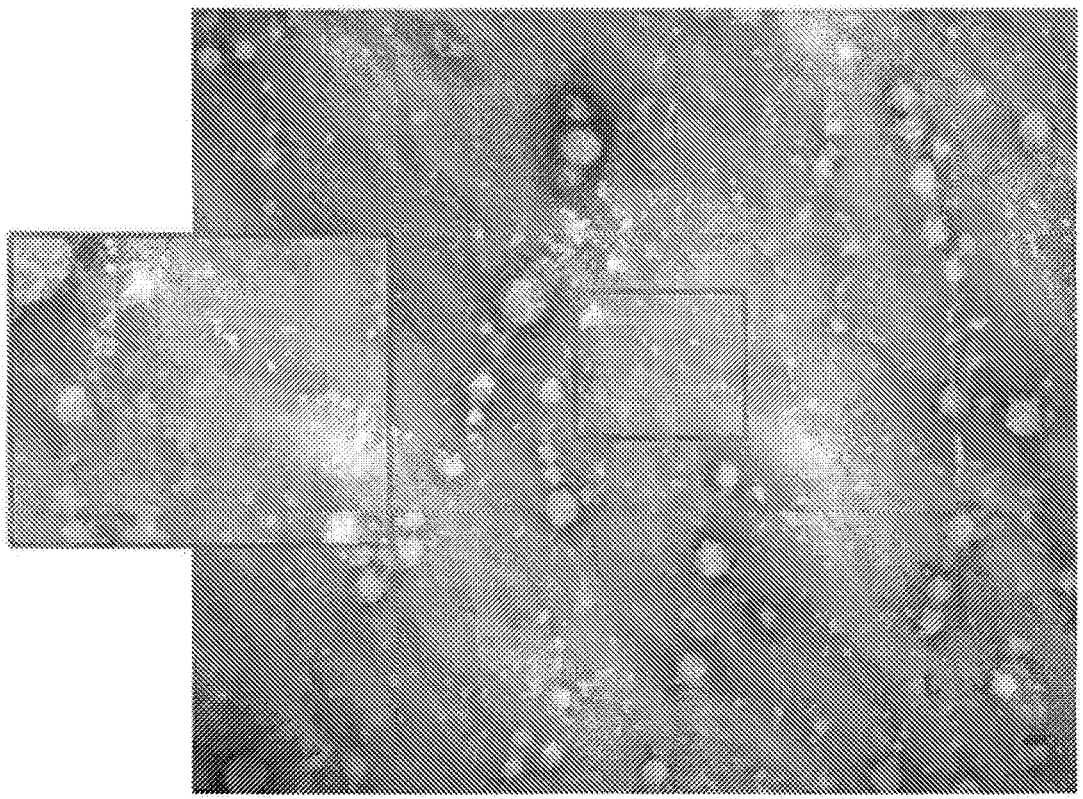

In FIGS. 9A and 9B, TEM images of HPV18 L1 capsomeres were captured before lyophilization (A) and after lyophilization and reconstitution (B).

Figure 10A:
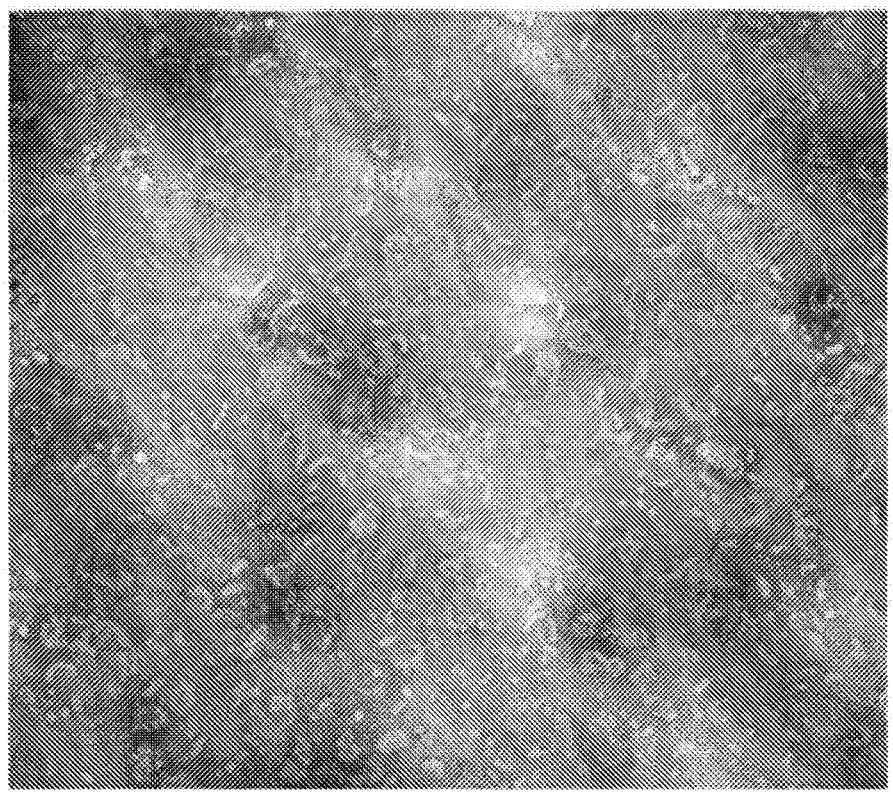
Figure 10B:
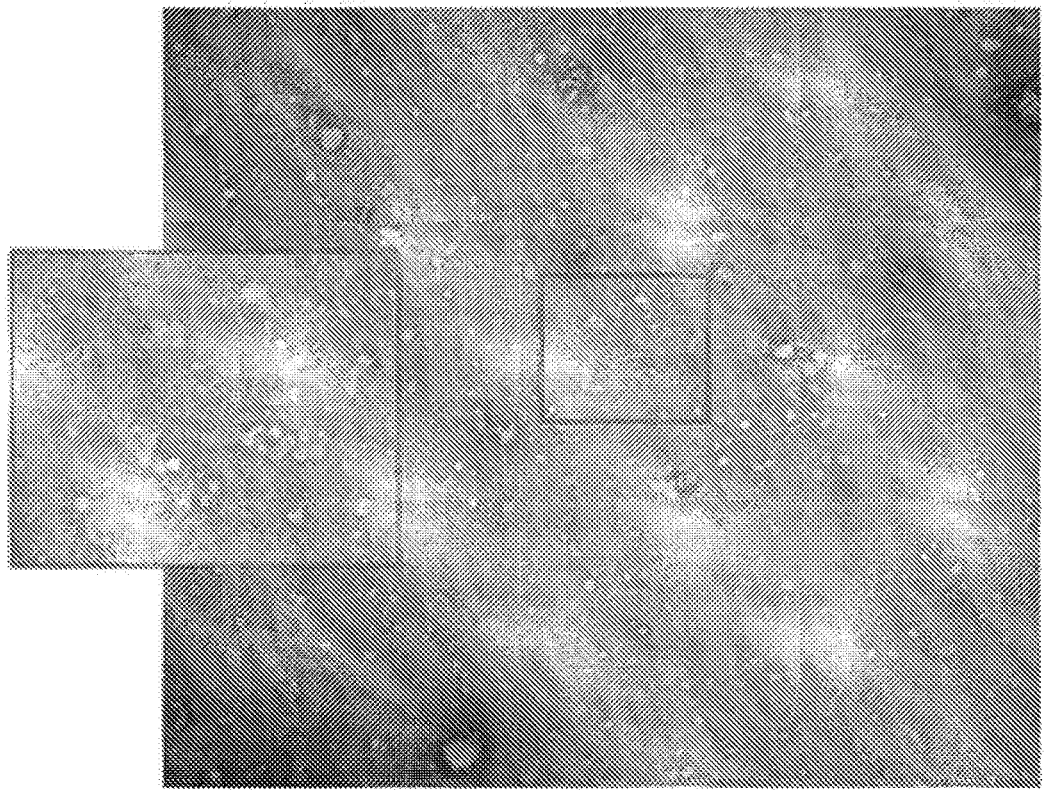

In FIGS. 10A and 10B, TEM images of HPV31 L1 capsomeres were captured before lyophilization (A) and after lyophilization and reconstitution (B).

Figure 11A:
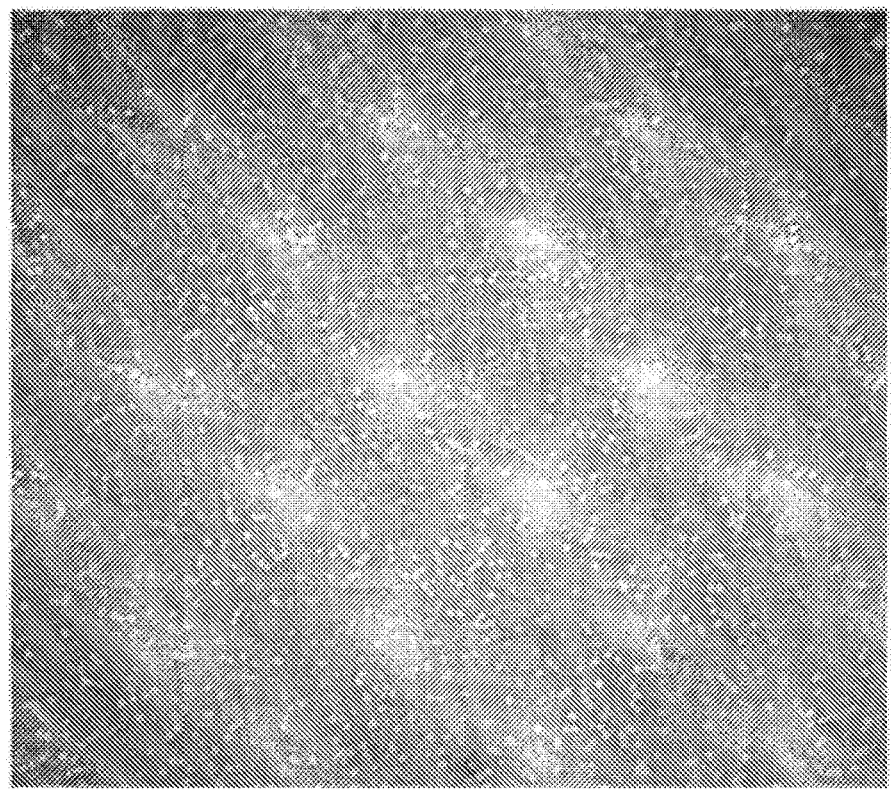
Figure 11B:
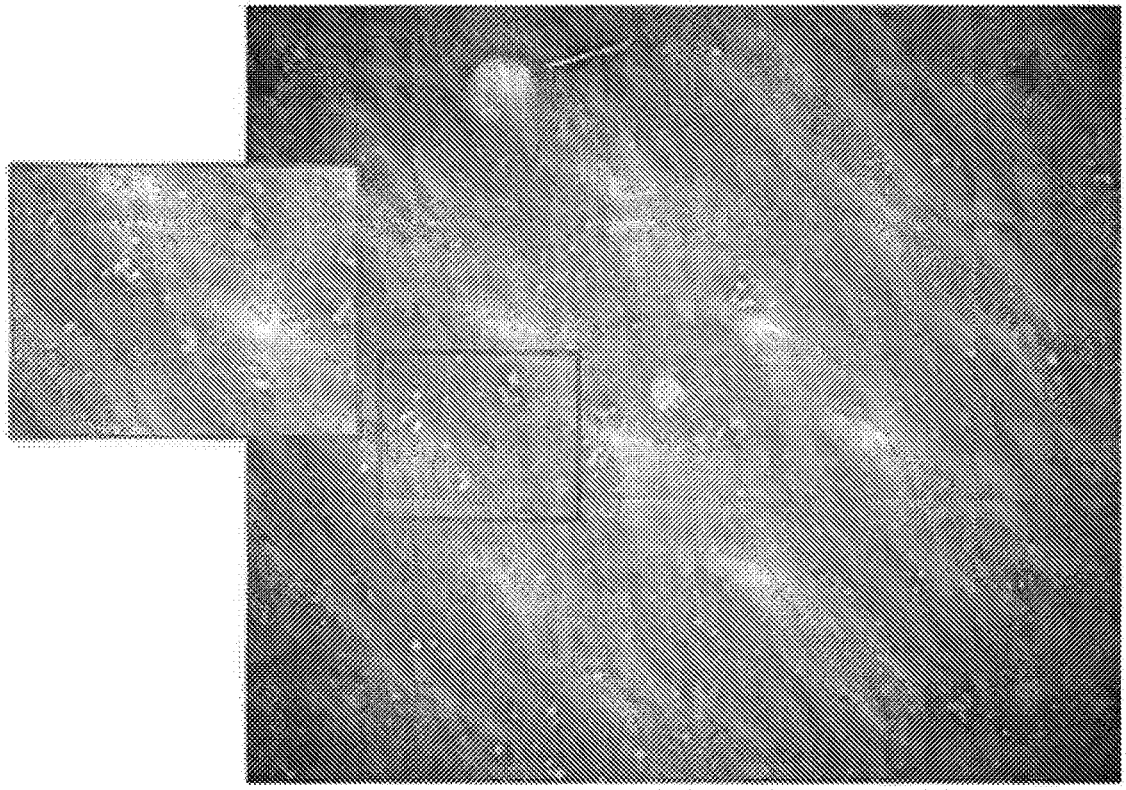

In FIGS. 11A and 11B, TEM images of HPV45 L1 capsomeres were captured before lyophilization (A) and after lyophilization and reconstitution (B).

Figure 12:
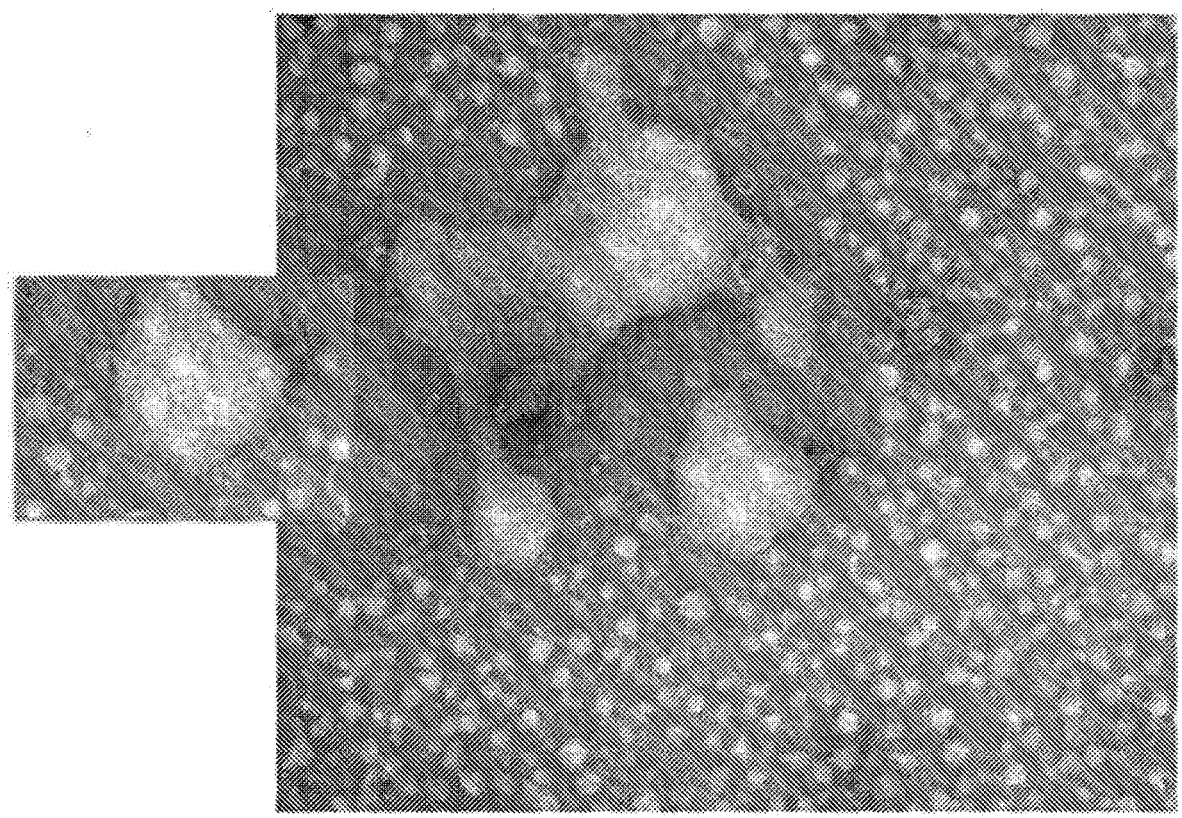

In FIG. 12, TEM images of a tetravalent vaccine formulation containing HPV16 L 1, HPV18 L1, HPV31 L1, and HPV45 L1 capsomeres were captured after lyophilization and reconstitution. These data demonstrate that all of the above HPV vaccine formulations exhibited the pentameric conformation of the HPV capsomere throughout the lyophilization and reconstitution process.

As illustrated in FIGS. 13A and 13B, vaccine formulations containing HPV16 L1, HPV18 L1, HPV31 L1, or HPV45 L1 capsomeres were subjected to SDS Page and Western Blot analysis before lyophilization (A), and after lyophilization and reconstitution (B). Additionally, as illustrated in FIG. 13C, a tetravalent formulation comprising HPV16 L1, HPV18 L1, HPV31 L1, and HPV45 L1 capsomeres of HPV16 L1, HPV18 L1, HPV31 L1, and HPV45 L1 capsomeres was also subjected to SDS Page and Western Blot analysis before lyophilization ("PRE") and after lyophilization and reconstitution ("POST"). For Western Blot analysis, a protein ladder was included in the lane directly to the left of each of the vaccine formulation samples. These data demonstrate that the pentameric conformation of each of the above HPV vaccine formulations was conservation the throughout lyophilization and reconstitution process.

Example 5

In certain exemplary methods, broad-spectrum HPV immunogenic compositions were tested in various formulations for stability at elevated temperatures. In one method, an ELISA assay was performed to assess titer of various formulations subjected to lyophilization and storage for prolonged stability. In exemplary FIG. 14, immune sera samples raised against lyophilized and reconstituted formulations of an exemplary construct, RG1-VLP that had been stored under various temperature conditions were tested by an HPV16 L1-VLP and RG1 peptide ELISA in 4-fold serial dilutions (1:200-1:204,800). Rabbit sera raised against HPV16 L1-VLP and RG1-VLP, and a BPV L1-raised monoclonal antibody, were used as positive or negative controls. Titers were graded positive for mean OD values greater than OD of pre-sera+3 standard deviations. n.d. indicate not determined. See FIG. 14 where stability is demonstrated at various temperatures up to an elevated temperature of about 50° C.

As illustrated in FIG. 14, titers were maintained at all temperatures tested.

Example 6

In another exemplary method, a pseudovirion-based neutralization assay (PBNA) was performed after storage of the HPV constructs at various temperatures and times. As illustrated in FIG. 15A and FIG. 15B L 1-PBNA (See for example, Buck 2004, 2005) was performed to detect neutralizing antibodies against hr. HPV16, and cross-neutralizing antibodies against hr. HPV18, 31, 39 and cutaneous Beta type HPV5. L2-PBNA (See for example Day 2012) was performed against HPV39 and HPV5 to more sensitively detect potential cross-neutralization, and improved antibody titers detected were demonstrated (See the bold print). Surprisingly, cross-neutralizing titers against multiple HPV types such as HPV types 8, 18 31 and 39 were enhanced (instead of reduced) after a thermal treatment consisting of incubation for 1 month at 50° C.

Example 7

Figure 16:
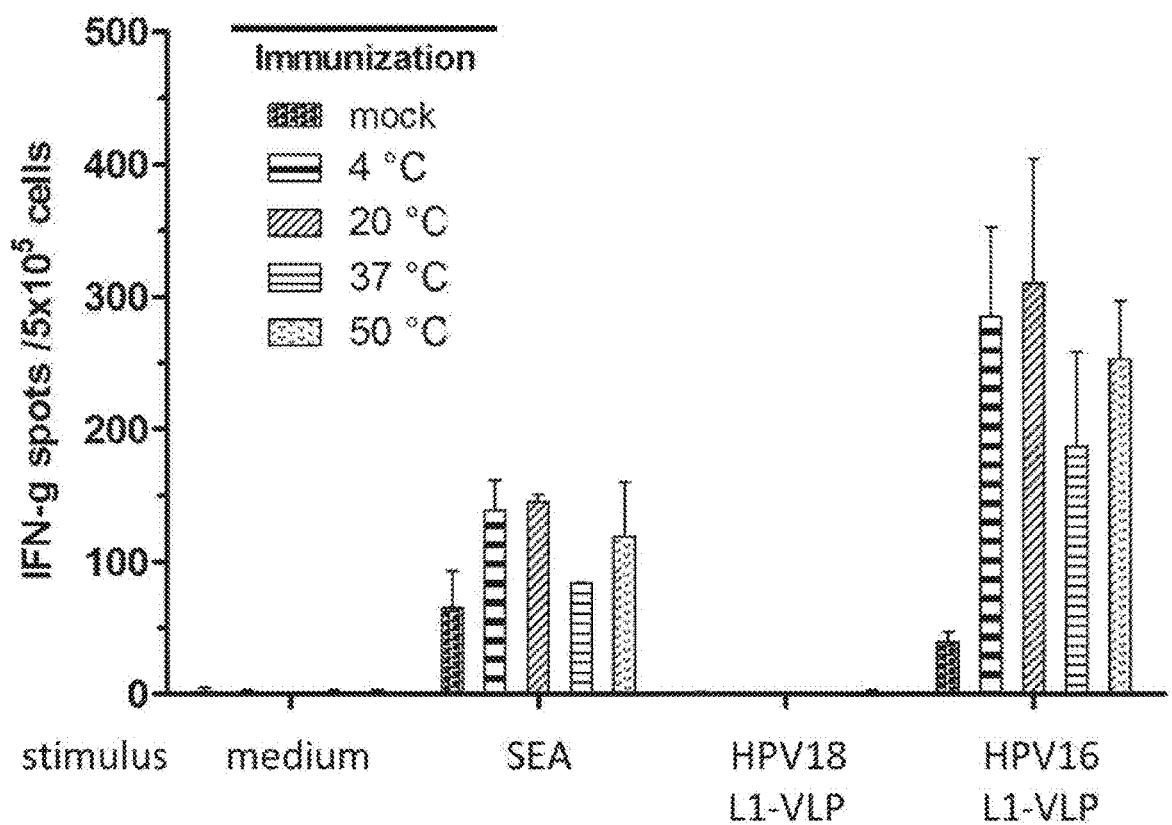

In another exemplary method, splenocytes were harvested from groups immunized with lyophilized RG1-VLP in certain exemplary compositions stored for 1 month at 4° C., 20° C., 37° C. or 50° C. and ex vivo stimulated with either HPV16 or HPV18 L 1 -VLP, or medium and Staphylococcus aureus enterotoxin A (SEA) as controls. Evaluation was performed using an ImmunoSpot® Analyzer (CTL) and Immunospot Software 5.0. (See for example, FIG. 16)

It was demonstrated in these exemplary methods that high-titer antibodies directed against HPV16 L1-VLP and the RG1 peptide were detected in all lyophilized RG1-VLP-raised immune sera by ELISA (FIG. 14). Notably, antibody titers were maintained even when lyophilized RG1-VLP were stored at elevated temperatures. Immune sera were neutralizing by L1-PBNA against HPV16 (titers of 3,200-51,200) and cross-neutralizing against hr HPV18, 31 and 39, and Beta HPVS (titers ranging from 50-3,200) in the majority of temperature groups (FIGS. 15A and 15B). Improved cross-neutralization was detected by more sensitive L2-PBNA particularly against HPV39 (titers of 50-800) and for some groups against HPVS (titers of <50-200). In this example, following incubation at higher temperatures lyophilized RG1-VLP maintain the ability to induce (cross-) neutralization with a trend towards reduced cross-neutralization seen in the highest temperature group (50° C.). By ELISPOT (FIG. 16), IFNy was induced by stimulation of splenocytes with HPV16 L 1 -VLP, but not HPV18 L1-VLP, in all tested storage temperature groups, which indicates maintained ability to raise a T cell response regardless of storage temperature of the RG1-VLP.

Example 8

Preparation of Lyophilized RG1-VLPs in Thermostable Glassy Matrices

Figure 17:
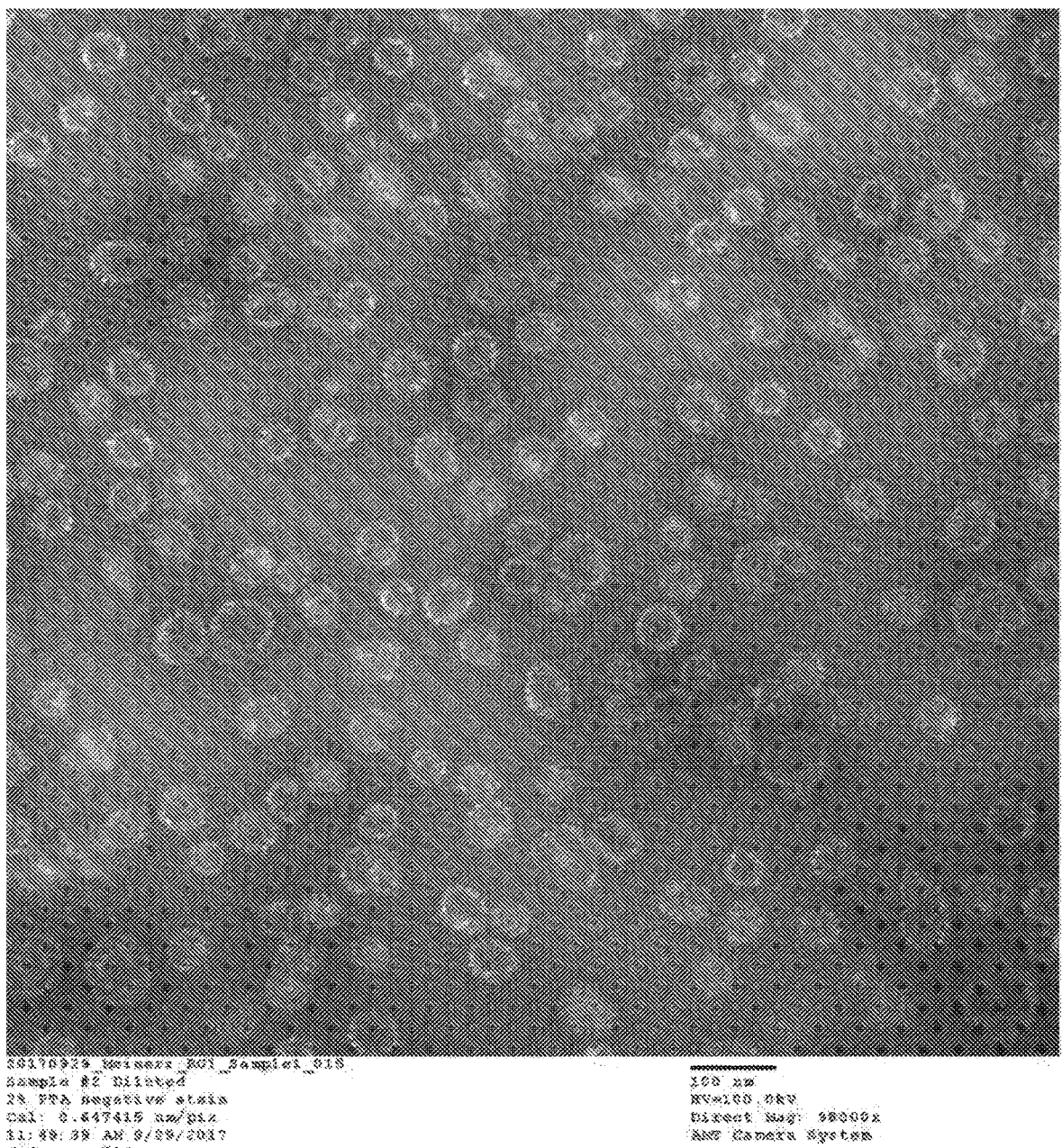

In one exemplary method, RG1-HPV VLPs were buffer-exchanged into a solution containing 100 mM histidine, pH7.1 Scanning electron micrographs (See FIG. 17) of the RG1-HPV VLP solutions revealed the presence of intact virus-like particles, with spiky protuberances. The solutions of RG1 HPV16 VLPs were mixed with trehalose and alum to form a mixture containing 10 wt/vol % trehalose, 0.5 mg/mL Alhydrogel® alum microparticles, and 0.1 mg/mL RG1 HPV VLPs. Other solutions were prepared in a similar fashion, but additionally contained 0.05 mg/mL of the immune co-stimulatory agent monophosphoryl lipid A. 1 mL aliquots of the solutions were filled into 3 mL Schott Fiolax lyophilization vials. The vials were placed on pre-cooled (-40° C.) shelves of a Lyostar pilot- scale lyophilizer. Samples were dried under vacuum (60 mTorr) and vials were sealed under nitrogen. Samples of the lyophilized formulations were stored in temperature-controlled incubators at 4, 20, 37 and 50 ° C. for a period of 1 day, 1 week, and 1 month. After storage, samples were reconstituted with 1 mL of water for injection, and 100 microliter doses of the resulting solution were administered to mice. FIG. 4 represents an exemplary image of a scanning electron micrograph of RG1-HPV VLPs demonstrating intact virus-like particles after buffer exchange into 100 mM histidine, pH 7.1

Materials and Methods

High purity a,a-trehalose dihydrate and sulfuric acid were purchased from Mallinckrodt Baker (Phillipsburg, N.J.). Histidine HCl, triethanolamine, and bovine serum albumin (BSA) were purchased from Sigma-Aldrich (St. Louis, Mo.). Two percent ALHYDROGEL (aluminum hydroxide adjuvant) was obtained from Accurate Chemicals and Scientific Corp (Westbury, N.Y.). Lyophilized synthetic monophosphoryl lipid A (glycopyranoside Lipid A (GLA) adjuvant) was purchased from Avanti Polar Lipids, Inc. (Alabaster, Ala.). Three mL 13 mm glass lyophilization vials, caps and seals were from West Pharmaceutical Services (Lititz, Pa.). Concentrated 10x phosphate buffered saline (PBS), TWEEN 20, and sodium chloride were from Fischer Scientific (Fair Lawn, N.J.). Water for injection was purchased from Baxter Healthcare Corporation (Deerfield, Ill.). Peroxidase-conjugated affinipure donkey anti-mouse IgG (H+L) was from Jackson ImmunoResearch Laboratories, Inc. (West Grove, Pa.). 3,3',5,5'-tetramentylbenzidine (TMB) was from Thermo Scientific (Rockford, Ill.).

HPV 16 L1 Capsomere Protein Purification

HPV 16 L1 capsomere protein was expressed in HMS174 E. coli containing the plasmid HPV16-p3 grown in terrific broth. Cells were lysed by two passages through a NIRO PANDA homogenizer at 800-1000 bar. The soluble portion was collected after centrifugation of cell lysate. Anion exchange was conducted by loading the soluble fraction onto a Q FAST FLOW column (GE Healthcare, Piscataway N.J.). The L1 protein, collected in the flow through was then precipitated out using ammonium sulfate precipitation at 30% saturation. The resuspended ammonium sulfate precipitate was solubilized in a tris buffer and passed once through the NIRO PANDA homogenizer at—500 bar. The homogenate was then loaded onto a Q sepharose anion exchange column (GE Healthcare, Piscataway, N.J.) and then eluted with a sodium chloride gradient. Collected fractions containing the L1 protein were exchanged into a 100 mM histidine buffer pH 7.1 by size exclusion chromatography.

Vaccine Formulation

Vaccines were formulated to contain 0.1 mg/mL HPV 16 L1 capsomere, 0 or 0.5 mg Al/mL from ALHYDROGEL, 0 or 0.05 mg GLA/mL in 54 mM histidine HCl pH 7.1 with 9.5 w/v % trehalose. Formulations were created to contain capsomere protein alone (protein), capsomere protein adsorbed to aluminum hydroxide (protein+alum) or capsomere protein adsorbed to aluminum hydroxide with GLA (protein+alum+GLA). Formulations were rotated end over end in 2 mL tubes for one hour to assure complete adsorption of protein to adjuvant.

Lyophilization

In certain examples, vaccines formulated with trehalose (other carbohydrate agents can substitute for trehalose such as sucrose, chitosan etc.) were lyophilized with 1 mL of formulation per vial. Lyophilizer shelves were pre-cooled to −10° C. (FTS Systems Lyophilizer, Warminster, Pa.) and vials were placed on the shelves. Vaccine formulations were surrounded by vials filled with DI water to minimize radiative heat transfer effects for vials near the edge of the lyophilizer shelves. The shelf temperature was decreased at a rate of 0.5° C./min to −40° C. and then held at −40° C. for 1 hour to allow the samples to completely freeze. Primary drying was initiated by decreasing the chamber pressure to 60 mTorr and increasing the shelf temperature to −20° C. at a rate of 2° C./min. Samples were held at −20° C. for 20 hours. Secondary drying was conducted by increasing the shelf temperature to 0° C. at a rate of 0.2° C./min, followed by an increase to 30° C. at a rate of 0.5° C./min and holding the shelf temperature at 30° C. for 5 hours. After drying, the shelf temperature was returned to 25° C. and the chamber was back-filled with nitrogen until atmospheric pressure was reached. Chlorobutyl rubber stoppers were inserted into vials under a nitrogen atmosphere. Before storage at −80° C., vials were sealed with aluminum caps.

Elevated Temperature Incubation Study

To test the stability of vaccines at an elevated temperature, liquid and lyophilized vaccines were stored at 50° C. for 0 or 12 weeks. Time 0 lyophilized vaccines refer to vaccines used immediately after removal from storage at −80° C.

Particle Size Analysis

Particles greater than 2 microns were measured by use of the FLOW-CAM (Fluid Imaging Technologies, Yarmouth, Me.). A 100 micron flow cell was used at a flow rate of 0.08 mL/min with images taken at a rate of 10 frames per second. A 10× objective and collimator were used. Light and dark settings of 17 and 15, respectively, were used to capture particles. Formulations were diluted ten times for placebo formulations, and 100 times for formulations containing protein. A sample volume of 0.35 mL was used for all formulations.

Differential Scanning Calorimetry (DSC)

Onset glass transition temperatures of placebo lyophilized formulations were obtained using differential scanning calorimetry (Diamond DSC, Perkin Elmer, Waltham, Mass.). Triplicate samples were prepared inside an aluminum pan under dry nitrogen. Pans were cycled twice between 25° C. and 150° C. at a scan rate of 100° C./min. The second heating scan was used to determine the onset glass transition temperature.

Transmission Electron Microscopy (TEM)

In other methods, vaccine or immunogenic formulations were adsorbed to carbon-coated grids and negative stained with 2% uranyl acetate. Images were collected using a transmission electron microscopy. Samples of vaccines containing one of each of the four capsomere types as well as samples of the tetravalent vaccine formulation that contained all four types, were analyzed by TEM before and after lyophilization. Because aluminum hydroxide microparticles can interfere with TEM analysis of capsomeres, samples tested with TEM did not contain aluminum hydroxide. In certain examples, vaccine formulations were adsorbed to formvar/carbon-coated, glow-discharged 400 mesh copper TEM grids. After sample adsorption, grids were washed with 5 mM EGTA and stained with 1-2% uranyl acetate. Images were collected using a Philips CM10 transmission electron microscope operating at 80 kV equipped with a GATAN BIOSCAN2 digital camera.

Size Exclusion Chromatography (SEC)

HPV 16 L1 capsomere protein was run on a SUPERDEX 200 INCREASE 10/300 GL column (GE Healthcare Life Sciences) in a buffer containing 50 mM Tris, 350 mM sodium chloride, 10% glycerol, 5 mM DTT at pH 8.1.

Fluorescence Melting Curve

Fluorescence melting curves were created to determine the protein melting temperature. Approximately 200 µL of 0.1 mg/mL HPV 16 L1 capsomere was placed in a micro quartz cuvette. Fluorescence spectra were collected from about 305 to 400 nm after being excited at 295 nm on a SLM Instruments Inc. fluorimeter (Urbana, Ill.). Spectra were recorded every 5° C. from 20° C. to 90° C., after an equilibration time of ten minutes. Center of spectral mass calculations were used to create the melting curve.

Front Face Fluorescence

Three mL of vaccine formulation was placed in a quartz cuvette in a front face geometry holder with angle of incidence of 53° on a fluorimeter. Samples were excited at 295 nm and the emission spectrum was collected from 310 nm to 400 nm. The peak intensity at 331 nm for time 0 samples and 340 for unfolded protein was monitored as acrylamide was added. The Stern-Volmer constant was measured by solving the following equation: $Fo/F=1+Ksv[Q]$. F0 is the fluorescence intensity without the quencher acrylamide, F is the fluorescence with the quencher present, Ksv is the Stern-Volmer constant and [Q] is the quencher concentration. The maximum Ksv value of this setup was found using free tryptophan at 0.1 mg/mL and the maximum Ksv value for the HPV 16 L1 capsomere was found by unfolding the protein overnight in 8M urea.

L1 and V5 Epitope Binding Assay

To determine the conservation of the L1 and V5 capsomere epitopes, an ELISA based assay was conducted. Vaccine formulations with and without aluminum hydroxide adjuvant were diluted in PBS such that 0.25, 0.125, 0.0625, and 0 µg/well of HPV 16 L1 capsomere protein was coated on 96-well Nunc flat bottom PolySorp Immuno plates and incubated overnight at 4° C. Plates were washed three times with 0.05% TWEEN 20 in PBS at 300 µL/well. Plates were blocked with 100 µL/well of blocking buffer (5% dry milk, 0.05% TWEEN 20 in PBS) for 1 hour at 37° C. After blocking, blocking buffer was removed and primary antibodies, against either L1 or V5 at a dilution of 1:1000 in blocking buffer, were added 50 µL/well and incubated at 37° C. for 1 hour. After washing three times, secondary antibody diluted 1:5,000 in wash buffer (0.05% TWEEN 20 in PBS) was added 50 µL/well and incubated at 37° C. for 1 hour. The secondary antibody for L1 and V5 respectively was a goat anti-rabbit and a goat anti-mouse HRP conjugated IgG antibody. After washing five times, 50 µL/well of Turbo TMB was added and plates were incubated at room temperature for five minutes. The reaction was quenched with 50 µL/well 1 M sulfuric acid and plates were read for absorbance at 450 nm on a Molecular Devices Kinetic Microplate Reader (Sunnyvale, Calif.).

Vaccine Immunogenicity

Murine studies were conducted under the University of Colorado at Boulder Institutional Animal Care and Use Committee (IACUC) protocol #1209.02. Female Balb/c mice from Taconic (Hudson, N.Y.) were allowed to acclimate at least one week before use and were 10-11 weeks old at the start of the immunization study. Mice had blood samples collected under isofluorane anesthesia on days 0, 21 and 36 through the retro orbital cavity, and were injected intramuscularly on days 0 and 21 with various formulations. Mice were injected with reconstituted lyophilized protein, protein+alum, protein+alum+GLA vaccines, and liquid GARDASIL and CERVARIX vaccines. Serum was separated by centrifugation at 10,000 rpm for 14 minutes at 4° C. and stored at −80° C. until use.

Total Antibody Enzyme Linked Immunosorbent Assay (ELISA)

NUNC MAXISORB 96 well plates (Thermo Fischer Scientific, Rochester, N.Y.) were coated with 50 µL/well of 1 µg HPV 16 L1 capsomere/mL diluted in PBS and incubated at 2-8° C. overnight. Plates were washed 3 times with PBS containing 0.05% TWEEN 20. Plates were blocked with 300 µL/well of PBS with 1% BSA, incubated at room temperature for 2 hours, and washed again. Serum was initially diluted in PBS with 1% BSA, 0.05% TWEEN 20, 100-fold for serum collected on days 0, 500-fold for serum collected on day 14, and 1,000 or 5,000-fold for serum collected on Day 28 for mice injected without and with adjuvant respectively. A series of in-plate 2-fold dilutions were made for each sample. Plates were incubated for 1.5 hours at room temperature and washed. Approximately 40 µL of HRP-conjugated donkey anti-mouse antibody diluted 10,000 times was added to each well and incubated for 1.5 hours at room temperature with shaking, followed by washing. Approximately 40 µL TMB was added to each well and incubated for 15 minutes, followed by quenching with 40 µL of 2N sulfuric acid. Plates were measured at 450 nm on a MOLECULAR DEVICES Kinetic Microplate Reader (Sunnyvale, Calif.).

To determine titers, average OD 450 values as a function of dilution were fit to a 4-parameter logistic equation using SigmaPlot software. The constraints 0<min<0.15 and max<3.3 were used. A cutoff value of 0.5 was used.

Pseudovirus Production

293TT cells were plated at a concentration of 7×106 cells/20 mL and allowed to adhere overnight. DNA plasmid for secreted alkaline phosphatase (SEAP), DNA plasmid for L 1 and L2 capsid proteins, and lipofectamine were incubated with OptiMEM-1 before being added to 293TT cells. Cells were incubated overnight with the DNA then harvested. TRITON-X, benzonase, plasmid safe, and ammonium sulfate were used to lyse cells. Pseudovirus was purified salt extraction, and collecting the supernatant after centrifugation. Clarified cell lysate was added to an OPTIPREP gradient and separated by centrifugation. Fractions were collected from the bottom of the gradient tube and assayed for DNA and protein content by PICOGREEN assays and BCA assay, respectively.

Neutralizing Antibodies

293TT cells were grown, harvested, and counted. 100 µL/well of 3×105 cells/mL were plated in 96 well tissue culture plates and incubated at 37° C. for 2-5 hours. Pseudovirus was added to dilutions of mouse serum and incubated on ice for 1 hour. Approximately 100 µL of pseudovirus/mouse serum solution was added to plated cells and incubated at 37° C. for 3 days. After incubation, supernatant was collected from cells. The GREAT ESCAPE SEAP Chemiluminescence test kit was used for detection of SEAP. Plates were read on a luminometer at a set glow-endpoint of 0.20 seconds/well. The neutralization titer is defined as the dilution of mouse serum that neutralizes greater than 50% of the pseudovirus.

SDS PAGE and Western Blots

Pre- and post-lyophilization samples of vaccines containing aluminum hydroxide adjuvant as well as HPV16 L1 capsomeres, HPV18 L1 capsomeres, HPV31 L1 capsomeres, or HPV45 L1 capsomeres sampled prior to lyophilization and after lyophilization and reconstitution were analyzed using Sodium Dodecyl Sulfate Polyacrylamide Gel Electrophoresis (SDS PAGE). A similar analysis was conducted for samples of a tetravalent vaccine formulation containing aluminum hydroxide as an adjuvant and a mixture of HPV16 L1 capsomeres, HPV18 L1 capsomeres, HPV31 L1 capsomeres and HPV45 L1 capsomeres. Samples were denatured by the addition of Sample Buffer (240mM Tris, 30% glycerol, 6% SDS, 6 mg/ml bromophenol blue and 15% P-mercapto ethanol [PMED and boiled at 95° C. for 10 minutes. Samples were loaded with constant volume and run at 150V, 150 mA for 1 hour and 10 minutes.

In certain examples, following electrophoresis, gels were placed in Transfer Buffer (250 mM Tris, 2M glycine, 20% methanol) for 20 minutes to remove SDS. Gels were transferred onto PVDF membrane for the Western blot using a semi-dry transfer unit (Hoefer, Holliston, Mass. ) at 15V for 45 minutes. Following transfer, the blot was blocked in a 5% milk solution in Tris Buffered Saline with Tween 20 (TBST) (10 mM Tris, 150 mM NaCl, 0.1% Tween 20) for one hour at room temperature. Primary antibody diluted in TB ST was added (GARDASIL treated rat sera, 1:5000 [HPV16 and 45]; a-HPV18 L1 mab specific for HPV18 L1, diluted 1:2000 [Abcam, Cambridge, MA]; a-HPV313G11C8 specific for HPV31 L, diluted 1:1000) and incubated with rocking at room temperature for one hour. The primary antibody was removed and the blot washed three times for 10 minutes each with TBST. An appropriate secondary alkaline phosphatase-conjugated antibody (diluted 1:5000 is TBST) was then added and incubated with rocking at room temperature for one hour. The secondary antibody was removed and the blot washed as before. The completed blot was developed in an alkaline phosphate developer (250 mM Tris, 250 mM NaCl, 12.5 mM MgCl2, 165 ug/ml 5-Bromo-4-chloro-3-indolyl phosphate [BCIP], 22 ug/ml nitro blue tetrazolium [NBT]) until bands were deemed sufficient. Blot was rinsed with deionized water to stop the developing reaction.

In certain methods, aluminum hydroxide (alum)-adjuvanted RGI-VLP were lyophilized by lyophilizing with trehalose. Aliquots of a dry-powder formulation were incubated at 4° C., 20° C., 37° C. or 50° C. for either 1 day, 1 week or 1 month, resuspended and used to immunize groups of Balb/c (n=5) in a 3-dose regime (211 g VLP/dose; week 0/2/4; blood finally drawn at week 6). Immune sera were pooled for groups and tested by HPV16 L1-VLP and RGI-peptide ELISA, as well as L1- and L2-based pseudovirion neutralization assays (LI- and L2-PBNA). Further, a T cell response was evaluated by IFNy ELISPOT using splenocytes that were pooled for groups.

All of the COMPOSITIONS and METHODS disclosed and claimed herein can be made and executed without undue experimentation in light of the present disclosure. While the compositions and methods have been described in terms of particular embodiments, it is apparent to those of skill in the art that variations maybe applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed is:

1. An essentially dried immunogenic composition comprising:
    a single broad-spectrum multi-targeted antigen complex of two or more different pathogens or serotypes, wherein the single complex comprises at least two assembled subunits from the two or more different pathogens or serotypes;

one or more aluminum salt adjuvants;

one or more immunologically-related co-stimulatory agents;

one or more non-reducing disaccharide agents selected from the group consisting of trehalose, sucrose, or a combination thereof;

one or more volatile salts, wherein the one or more volatile salts are selected from the group consisting of one or more of ammonium acetate, ammonium formate, triethylammonium acetate, triethylammonium formate, triethylammonium carbonate, trimethylamine acetate, trimethylamine formate, trimethylamine carbonate, pyridinal acetate and pyridinal formate, or combinations thereof; and wherein the essentially dried immunogenic composition excludes mannitol.

2. The immunogenic composition according to claim 1, wherein the two or more different pathogens or serotypes comprise two or more different viral, bacterial, or fungal pathogens or serotypes.

3. The immunogenic composition according to claim 1, wherein the one or more immunologically-related co-stimulatory agents comprise one or more Toll-like Receptor (TLR) agonists.

4. The immunogenic composition according to claim 3, wherein the one or more TLR agonists comprise one or more TLR4 agonists or TLR5 agonists.

5. The immunogenic composition according to claim 1, wherein the one or more immunologically-related co-stimulatory agents comprise one or more of lipid A, lipid A derivatives, monophosphoryl lipid A, chemical analogues of monophosphoryl Lipid A, CpG containing oligonucleotides, glycopyranoside lipid A (GLA), flagellin, flagellins derived from gram negative bacteria, fragments of flagellins capable of binding to TLR-5 receptors, saponins, analogues of saponins, QS-21, purified saponin fractions, ISCOMS and saponin combinations with sterols and lipids, or a combination thereof.

6. The immunogenic composition according to claim 1, wherein the one or more immunologically-related co-stimulatory agents comprise glycopyranoside lipid A (GLA).

7. The immunogenic composition according to claim 1, wherein the one or more non-reducing disaccharide agents is trehalose.

8. The immunogenic composition according to claim 1, wherein the one or more volatile salts comprise one or more of ammonium acetate, ammonium formate, or a combination thereof.

9. The immunogenic composition according to claim 1, wherein the composition is stable for one month or greater at elevated temperatures.

10. The immunogenic composition according to claim 1, wherein the at least two assembled subunits of the broad-spectrum multi-targeted antigen complex comprise two assembled subunits from two or more viruses, viral segments, viral peptides, viral epitopes, or viral fragments derived therefrom.

11. The immunogenic composition according to claim 10, wherein the single broad-spectrum multi-targeted antigen complex induces an immune response against the two or more different pathogens or serotypes represented in the single broad-spectrum multi-targeted antigen complex.

12. The immunogenic composition according to claim 1, wherein the at least two assembled subunits of the single broad-spectrum multi-targeted antigen complex comprises at least one chimeric viral complex or at least one live, attenuated viral complex.

13. The immunogenic composition according to claim 1, wherein the two or more pathogens or serotypes comprise at least one of a chimeric viral complex and a live, attenuated virus complex, comprising one or more of a multi-peptide cytomegalovirus (CMV)-modified vaccinia Ankara (MVA) complex, *Plasmodium falciparum* multiple-antigen peptide complex, PnuBioVax (PBV multi-antigen) complex, serotype-independent prophylactic complex against *S. pneumoniae* disease, ALVAC(2) complex, bacterial backed complex, flavivirus antigenic complex, or alphavirus antigenic complex or combinations thereof.

14. The immunogenic pharmaceutical composition according to claim 1, wherein the one or more volatile salts is ammonium acetate.

15. The immunogenic composition according to claim 1, wherein the two or more different pathogens or serotypes comprise at least one of a flavivirus, an alphavirus or a combination thereof.

16. The immunogenic composition according to claim 1, wherein the one or more non-reducing disaccharide agents is sucrose.

17. The immunogenic composition according to claim 1, wherein the essentially dried immunogenic composition is formulated for parenteral administration.

18. The immunogenic composition according to claim 1, wherein the single broad-spectrum multi-targeted antigen complex of two or more different pathogens or serotypes comprises two or more polynucleotides, or two or more polypeptides, or a mixture thereof from the two or more different pathogens or serotypes.

19. An immunogenic pharmaceutical composition of use as a vaccine comprising: the essentially dried immunogenic composition according to claim 1, and a pharmaceutically acceptable excipient.

20. A method of preparing an essentially dried immunogenic composition according to claim 1, the method comprising:

(a) combining a single broad-spectrum multi-targeted antigen complex of two or more different pathogens or serotypes, wherein the single complex comprises at least two assembled subunits of the two or more different pathogens or serotypes, with one or more aluminum salt adjuvants; one or more immunologically-related co-stimulatory agents; one or more non-reducing disaccharide agents selected from the group consisting of trehalose, sucrose, or a combination thereof; and one or more volatile salts wherein the one or more volatile salts are selected from the group consisting of one or more of ammonium acetate, ammonium formate, triethylammonium acetate, triethylammonium formate, triethylammonium carbonate, trimethylamine acetate, trimethylamine formate, trimethylamine carbonate, pyridinal acetate and pyridinal formate, or combinations thereof; in a buffer making a liquid immunogenic composition and wherein the liquid immunogenic composition excludes mannitol;

(b) freezing the liquid immunogenic composition; and (c) lyophilizing or drying the frozen immunogenic composition creating an essentially dry powder of the immunogenic composition.

21. The method according to claim 20, wherein the one or more immunologically-related co-stimulatory agents comprise one or more Toll-like Receptor (TLR) agonists.

22. The method according to claim 21, wherein the one or more TLR agonists comprises one or more TLR4 agonist or TLR5 agonist.

23. The method according to claim 20, wherein freezing comprises tray freezing, flash freezing, shelf freezing, spray-freezing, and shell-freezing.

24. The method according to claim 20, wherein the liquid immunogenic composition is prepared as a hypertonic mixture.

25. A method for eliciting an immune response to two or more different pathogens or serotypes in a subject, the method comprising administering to the subject a reconstituted immunogenic composition according to claim 19 and eliciting an immune response to the two or more different pathogens or serotypes in the subject.

* * * * *